US006304797B1

(12) United States Patent
Shusterman

(10) Patent No.: US 6,304,797 B1
(45) Date of Patent: Oct. 16, 2001

(54) AUTOMATED MEDICATION DISPENSER WITH REMOTE PATIENT MONITORING SYSTEM

(75) Inventor: Larry Shusterman, Merion Station, PA (US)

(73) Assignee: Rapid Patient Monitoring, L.L.C., Philadelphia, PA (US)

(*) Notice: Subject to any disclaimer, the term of this patent is extended or adjusted under 35 U.S.C. 154(b) by 0 days.

(21) Appl. No.: 09/126,662

(22) Filed: Jul. 30, 1998

Related U.S. Application Data

(60) Provisional application No. 60/054,403, filed on Jul. 31, 1997.

(51) Int. Cl.[7] ................................................. G06F 17/00
(52) U.S. Cl. .......................... 700/243; 700/242; 700/237; 700/236
(58) Field of Search .................... 700/231, 236, 700/241, 242, 244, 216, 222, 243; 221/2, 8, 9

(56) References Cited

U.S. PATENT DOCUMENTS

| | | |
|---|---|---|
| 3,534,727 | 10/1970 | Roman . |
| 4,494,553 | 1/1985 | Sciarra et al. . |
| 4,583,547 | 4/1986 | Granek et al. . |
| 4,695,954 * | 9/1987 | Rose ...................................... 364/413 |
| 4,709,704 | 12/1987 | Lukasiewicz . |
| 4,748,600 * | 5/1988 | Urquhart ................................. 368/10 |
| 4,763,810 | 8/1988 | Christiansen . |
| 4,785,969 * | 11/1988 | McLaughlin ............................ 221/2 |
| 4,827,943 | 5/1989 | Bornn et al. . |
| 4,838,275 | 6/1989 | Lee . |
| 5,012,411 | 4/1991 | Policastro et al. . |
| 5,014,875 * | 5/1991 | McLaughlin et al. ................... 221/2 |
| 5,036,852 | 8/1991 | Leishman . |
| 5,050,612 | 9/1991 | Matsumura . |

(List continued on next page.)

Primary Examiner—Christopher P. Ellis
Assistant Examiner—Michael E. Butler
(74) Attorney, Agent, or Firm—Ratner & Prestia

(57) ABSTRACT

A medication dispensing unit comprising a carousel defining a plurality of compartments, each of the compartments adapted to store a dose of medication is disclosed. The dispensing unit also comprises a housing that has a surface adapted to receive the carousel. The housing defines a receptacle and an access aperture that communicates between the receptacle and the surface that is adapted to receive the carousel. One of the compartments is positioned to communicate with the receptacle through the access aperture. The unit also comprises a dosing drawer that is positioned within the receptacle and communicates with the access aperture to receive a dose of medication from the compartment through the access aperture. The dosing drawer includes a normally closed trap door that, when opened, allows a dose of medication in the drawer to drop out of the dosing drawer. The dispensing unit comprises a recovery drawer that is positioned within the receptacle and communicates with the dosing drawer through the trap door, and receives a dose of medication from the dosing drawer when the trap door is opened. The medication dispensing unit also comprises means for rotating the carousel and a microcontroller that defines dosing period, determines that the patient has accessed the dosing drawer within a dosing period, and locks the recovery drawer.

7 Claims, 25 Drawing Sheets

U.S. PATENT DOCUMENTS

| | | | |
|---|---|---|---|
| 5,097,982 | * 3/1992 | Kedem et al. | 221/3 |
| 5,111,818 | 5/1992 | Suzuki et al. . | |
| 5,148,944 | 9/1992 | Kaufman et al. . | |
| 5,159,581 | 10/1992 | Agans . | |
| 5,176,285 | 1/1993 | Shaw . | |
| 5,200,891 | 4/1993 | Kehr et al. . | |
| 5,246,136 | 9/1993 | Loidl . | |
| 5,289,824 | 3/1994 | Mills et al. . | |
| 5,292,029 | 3/1994 | Pearson . | |
| 5,339,821 | 8/1994 | Fujimoto . | |
| 5,377,864 | * 1/1995 | Blechle et al. | 221/2 |
| 5,390,238 | 2/1995 | Kirk et al. . | |
| 5,392,952 | 2/1995 | Bowden . | |
| 5,408,443 | * 4/1995 | Weinberger | 368/10 |
| 5,431,299 | 7/1995 | Brewer et al. . | |
| 5,441,047 | 8/1995 | David et al. . | |
| 5,441,165 | 8/1995 | Kemp et al. . | |
| 5,462,051 | 10/1995 | Oka et al. . | |
| 5,472,113 | 12/1995 | Shaw . | |
| 5,511,553 | 4/1996 | Segalowitz . | |
| 5,522,525 | * 6/1996 | McLaughlin et al. | 221/4 |
| 5,558,638 | 9/1996 | Evers et al. . | |
| 5,562,232 | * 10/1996 | Pearson | 221/7 |
| 5,582,323 | * 12/1996 | Kurtenbach | 221/2 |
| 5,609,268 | * 3/1997 | Shaw | 221/2 |
| 5,646,912 | 7/1997 | Cousin . | |
| 5,865,342 | * 2/1999 | Ito et al. | 221/265 |
| 5,905,653 | * 5/1999 | Higham et al. | 364/479.14 |
| 5,971,594 | * 10/1999 | Sahai et al. | 364/479.12 |

* cited by examiner

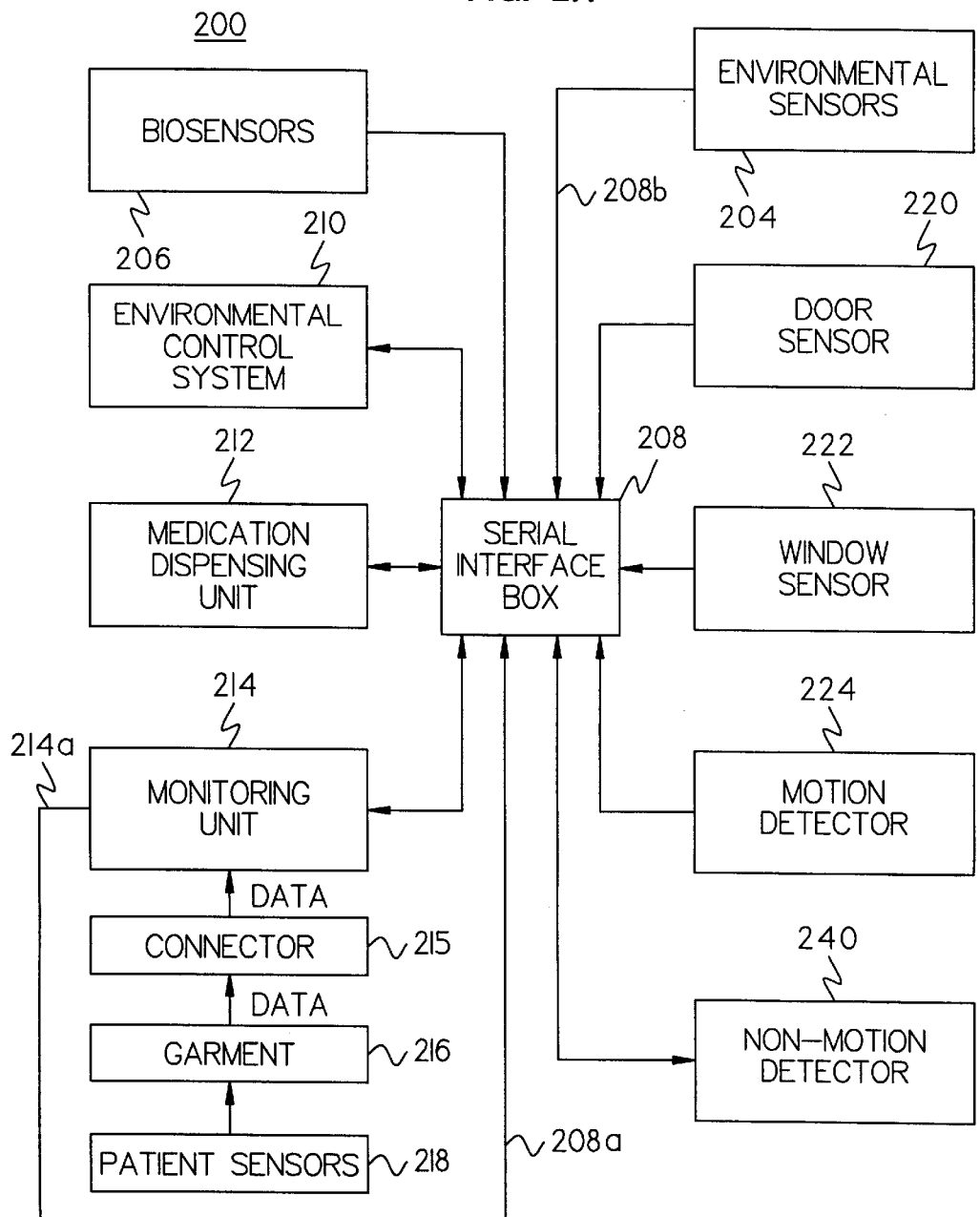

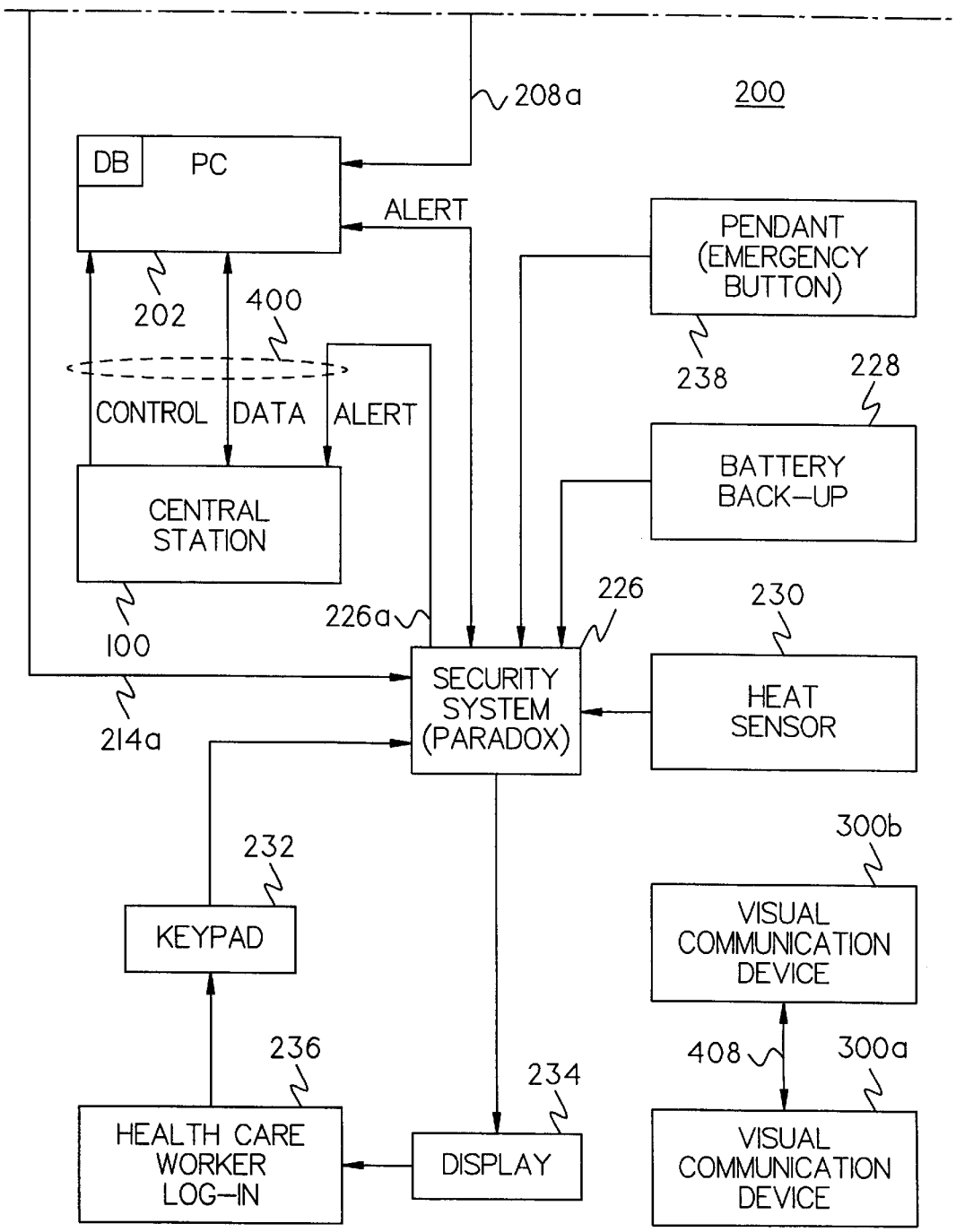

| FIG. 4A |
|---|
| FIG. 4B |

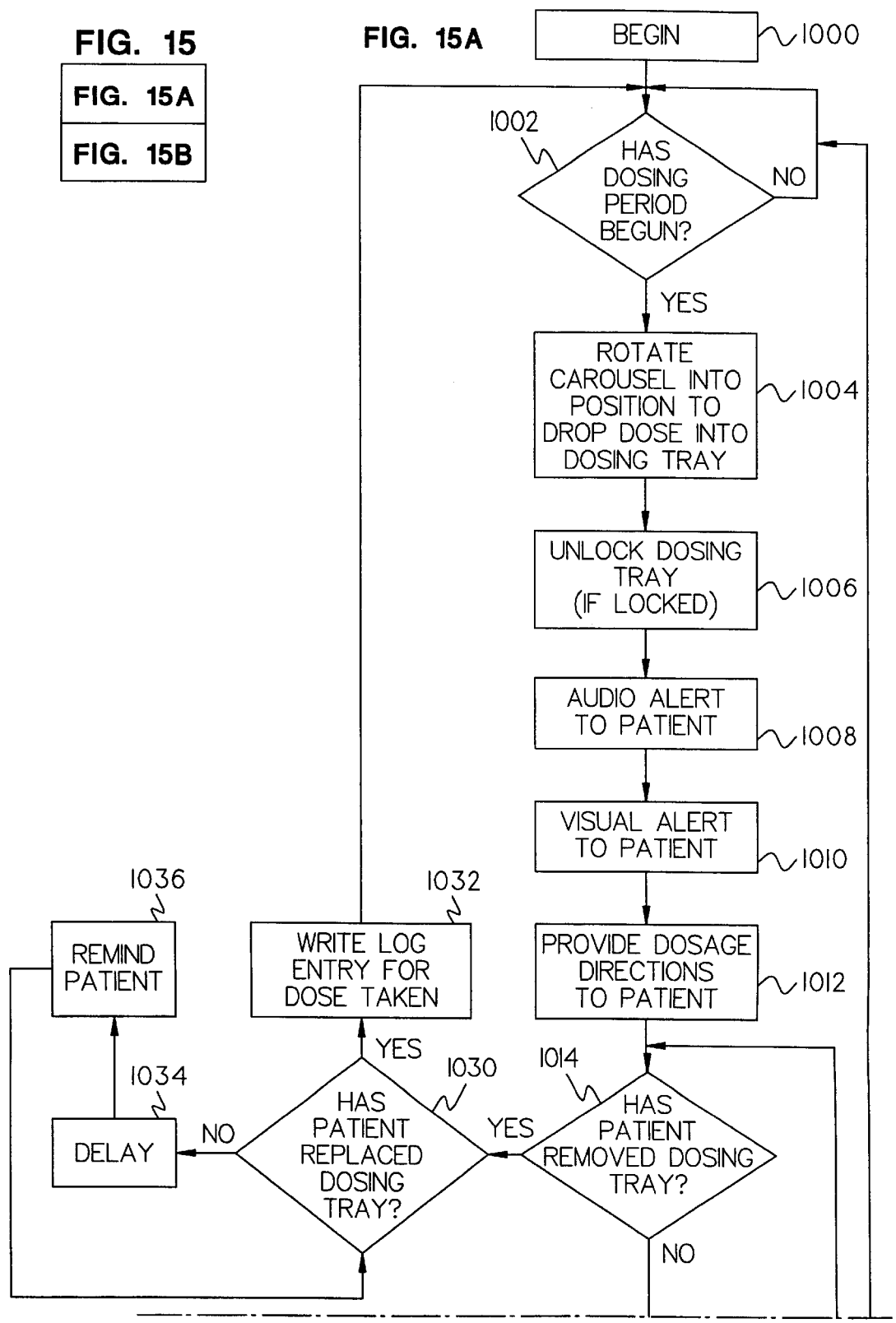

TIME STAMP
DOOR STATUS ~220
WINDOW STATUS ~222
MOTION DETECTOR STATUS ~224
NON-MOTION DETECTOR STATUS ~240
BIOSENSOR DATA ~206
    → OXYGEN SATURATION ~700
       ECG WAVEFORM ~702
       STETHOSCOPE READING ~704
       GLUCOMETER READING ~706
       SPIROMETER READING ~708
ENVIRONMENTAL SENSOR DATA ~204
    → ROOM TEMPERATURE ~710
       ROOM HUMIDITY ~712
       BAROMETRIC PRESSURE ~711
       CARBON MONOXIDE LEVEL ~714
       SMOKE OR OTHER IMPURITIES ~716
PATIENT MONITORING UNIT ~214
    → PULSE RATE
       RESPIRATION RATE
       BLOOD PRESSURE

FIG. 17

| PREDEFINED MESSAGE IDENTIFIER | VERSION IN LANGUAGE A | VERSION IN LANGUAGE B | ... | VERSION IN LANGUAGE N |
|---|---|---|---|---|
| 1 | | | ... | |
| 2 | | | ... | |
| 3 | | | ... | |
| 4 | | | ... | |
| 5 | | | ... | |
| ... | ... | ... | ... | ... |
| M | | | ... | |

| EVENT | PREDEFINED MESSAGE IDENTIFIER |
|---|---|
| 1 | 5 |
| 2 | 2 |
| 3 | 6 |
| 4 | 1 |
| ⋮ | ⋮ |
| M | M |

AUTOMATED MEDICATION DISPENSER WITH REMOTE PATIENT MONITORING SYSTEM

This application claims benefit of Prov. No. 60/054,403 filed Jul. 31, 1997.

FIELD OF THE INVENTION

This invention pertains generally to patient monitoring, and more specifically to monitoring patient status and communicating with a patient from a point remote from the patient's location.

BACKGROUND OF THE DISCLOSURE

An ongoing concern in the medical profession is the containment of labor costs, especially the cost of nursing and other patient monitoring personnel. One way to minimize costs is to find ways to allow fewer nurses to monitor larger numbers of patients without jeopardizing patient safety. In addition, hospitals are discharging patients earlier, allowing them to recuperate at home rather than in the hospital. In a typical hospital setting, nurses must periodically check the patients' vital signs, to administer doses of medicine, and to attend to requests or problems reported by patients. Where patients are recuperating at home or in far-flung branches of a large hospital, however, it is especially difficult for nursing personnel to monitor those remote patients in a cost-effective manner.

Another concern in the medical profession is the accurate administration of prescription medication to patients. Typically, prescription medicine is administered at periodic dosing intervals during a day. These dosing intervals are determined by a dosing schedule established by a treating physician. Medical support personnel administer doses of medication by retrieving the prescribed doses from bulk medicine supplies at the hospital pharmacy. This approach is inefficient and error-prone, because the support personnel often split time between administering medication and performing other duties. Further, to the extent that records of medication doses are kept, those records of medication doses are kept manually by the support personnel themselves. If the personnel are hurried, they may not keep accurate records of medication doses. In addition, the medication doses may not be correct because a harried support person failed to fill the prescription properly.

Yet another concern is the precise placement of the various sensors used to sense a patient's vital signs through physical contact with the patient's body. For example, an EKG sensor operates by sensing electrical activity within the body, and must be placed strategically on the body best to detect this electrical activity. Similarly, other types of sensors must be placed carefully and precisely for optimum sensing effectiveness. In the context of remote patient monitoring, it is desirable to avoid requiring medical support personnel to travel to the patient's location to place and check the various sensors located on a patient's body. Imposing the expense of such travel on medical support personnel could outweigh any benefits realized by having the patient recuperate at a site remote from the hospital.

SUMMARY OF THE INVENTION

The present invention provides an integrated patient monitoring system that includes a garment, a monitoring device, and a medication-dispensing unit. The garment is adapted for wearing by a patient, and is adapted to place at least one sensor in communication with the patient's body. The garment includes a connector communicating with the sensor. The monitoring device communicates with the sensor through the connector, and records signals from the sensor. The monitoring device also exchanges signals representing patient status with a central station. Preferably, the patient monitoring system restricts access to the monitoring device to authorized personnel. The medication-dispensing unit communicates with the monitoring device to receive commands from the monitoring device, and to transfer signals representing the status of medication doses to the monitoring device.

The garment of the invention includes at least one sensor, a torso portion adapted to fit the torso of a patient and defining at least one aperture to house the sensor, a sleeve portion adapted to fit the arm of the patient, and a connector communicating with the sensor. Either the torso portion or the arm portion defines a one channel linking the connector to the sensor. This channel houses a signal transmission conduit that couples the sensor to the connector.

The automated medication dispenser includes a carousel, a housing, a dosing drawer, a recovery drawer, and a microcontroller. The carousel defines a plurality of compartments, with each of the compartments adapted to store a dose of medication. The housing includes a surface adapted to receive the carousel, with the housing defining a receptacle and an access aperture communicating between the receptacle and the surface adapted to receive the carousel. A first one of the compartments is positioned to communicate with the receptacle through the access aperture. The medication dispenser provides means for rotating the carousel to position a second one of the compartments to communicate with the receptacle through the access aperture.

BRIEF DESCRIPTION OF THE DRAWINGS

The present invention is described by non-limiting examples with reference to the attached drawings, in which:

FIG. 2 is a block diagram of a remote site as shown in FIG. 1;

FIG. 17 is a diagram of an exemplary database record storing the data collected during the execution of the software illustrated in FIG. 16;

FIG. 25 is a diagram of an exemplary data structure used with the medication dispensing unit shown in FIG. 2 to support multi-lingual capability; and FIG. 26 is a diagram of an exemplary data structure used in conjunction with the data structure shown in FIG. 25 to enable the medication dispensing unit to provide messages in several different languages.

DETAILED DESCRIPTION OF EXEMPLARY EMBODIMENTS

Figure 1:
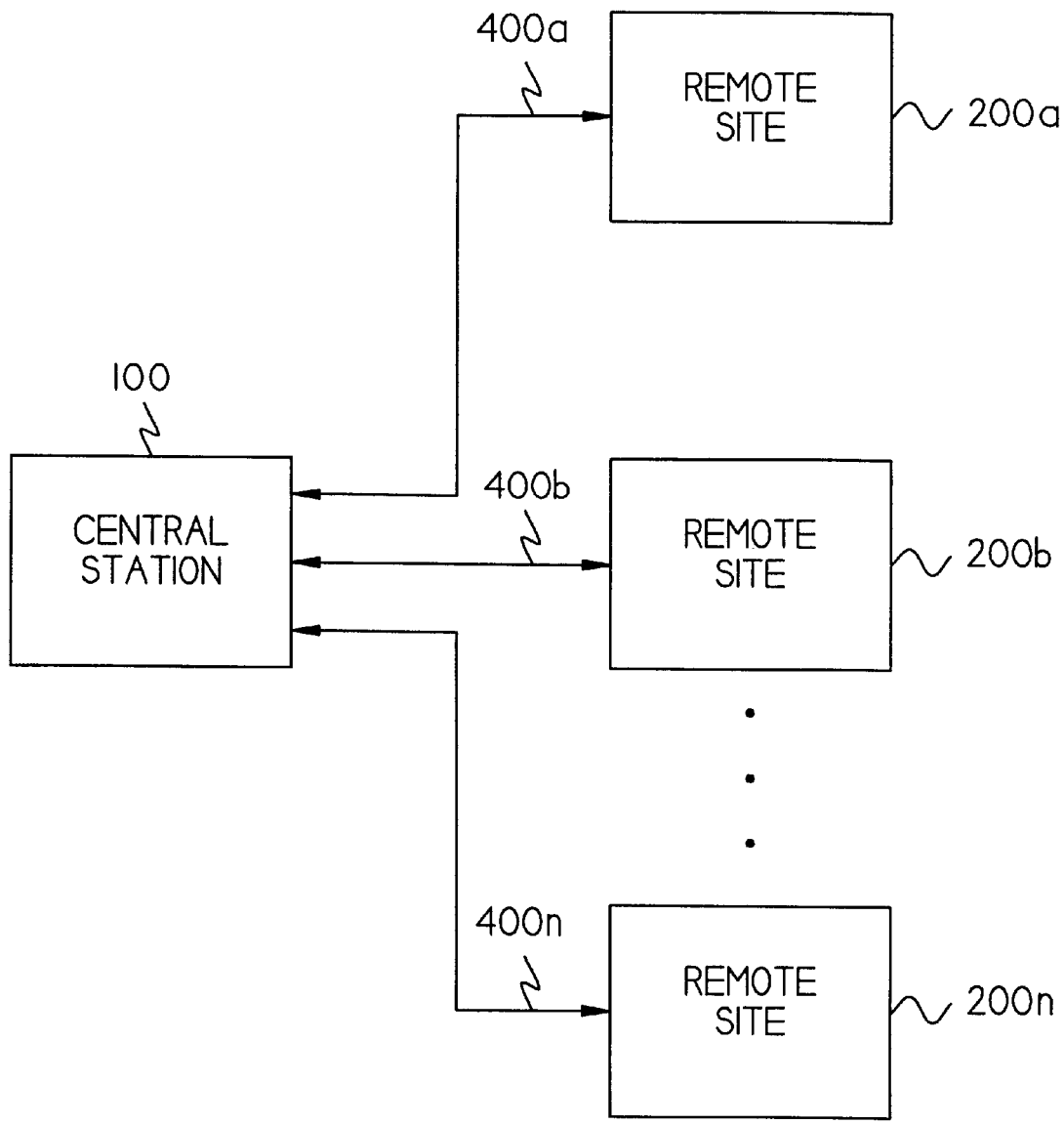
FIG. 1 is a block diagram of the remote patient monitoring system of the present invention.

FIG. 1 is a block diagram of a remote patient monitoring system 10 constructed in accordance with the present invention. In a minimum configuration, system 10 includes central station 100 and one remote site 200. However, the system 10 can be extended to include any number of remote sites 200, limited only by the computational resources provided by central station 100. FIG. 1 illustrates an exemplary and not limiting embodiment including a plurality of remote sites 200a, 200b, . . . 200n.

Central station 100 exchanges commands and data with each remote site 200 over a communication link 400. As shown in FIG. 1, communication link 400a couples central station 100 with remote site 200a, communication link 400b couples central station 100 with remote site 200b, and communication link 400n couples central station 100 with remote site 200n. It will be understood that for each remote site 200 provided by system 10, a communication link 400 will couple that remote site 200 to central station 100.

Using communication link 400, the central station 100 transmits commands and configuration data to each remote site 200, and receives data sampled and gathered at each remote site 200. Typically, central station 100 is located at a hospital or clinic, where patient support staff or nursing personnel are gathered. Remote site 200 is a patient location where patient status is to be monitored. A remote site 200 is typically located either at a patient's home or at a satellite location within a hospital or clinic. Remote site 200 could also be a patient bed area within a hospital or nursing home. System 10 allows personnel at central station 100 to remotely monitor and track multiple patients located at remote sites 200. According to several embodiments of the invention, the communication link 400 is implemented with POTS lines, ISDN lines, WANs, LANs, Intranet links, Internet links, a dial-up telephone line, or other communication lines.

The components and operation of central station 100 and an exemplary remote site 200 are described in more detail below.

FIG. 2 is a block diagram of a remote site 200 as shown in FIG. 1. It should be understood that in FIG. 2 and the other drawing figures, a single communication line is shown between certain entities for convenience of illustration. It should also be understood further that several parallel communication lines could be used in alternative embodiments.

In a minimum configuration, a remote site 200 includes a patient monitoring unit 214 and a garment 216 housing a plurality of sensors 218 and adapted to be worn by a patient. In this minimum configuration, patient monitoring unit 214 receives readings from sensors 218, and communicates these readings directly to central station 100. Patient monitoring unit 214 also receives commands from central station 100, for example to take readings from a specific one of sensors 218.

In the exemplary embodiment shown in FIG. 2, each remote site 200 includes at least a personal computer (PC) 202, a security system 226, a serial interface box 208, a patient monitoring unit 214, a medication dispensing unit 212, and a garment 216 adapted to be worn by a patient. Each of these components is described in detail below, along with their associated subcomponents. Depending on the requirements of a given remote site 200, one or more of the components shown in the exemplary embodiment of FIG. 2 can be omitted, such as environmental control system 210, medication dispensing unit 212, door sensor 220, window sensor 222, motion and non-motion detection sensors 224 and 240, or security system 226 and its related subcomponents.

PC 202 is coupled to central station 100 by communication link 400 to exchange control signals, data signals, and alert.signals with central station 100. In an exemplary embodiment, PC 202 is an IBM-compatible PC equipped with at least a Pentium™ microprocessor, approximately 128 Kb of memory, approximately 500 Mb of hard disk capacity, a serial port, and a communications modem of at least 28.8 baud capacity. It is within the scope of the invention to modify the specific configuration of PC 202 to support the remote site 200. Alternatively, PC 202 may be a personal-type computer manufactured by other vendors, such as Apple Corporation. As shown in FIG. 2, PC 202 exchanges both control and data signals with central station 100, and sends alert signals to central station 100 to command the attention of support personnel, when an emergency or other urgent condition occurs.

PC 202 operates with a suitable operating system, such as Windows NT, developed and sold by Microsoft Corporation of Redmond, Wash., and a database management package such as SQL Server, also developed and sold by Microsoft Corporation. The operating system running aboard the PC 202 supports multitasking, in an exemplary embodiment.

Serial interface box 208 is coupled to the serial port of PC 202. Because conventional PC architecture can monitor and service only a limited number of serial communication ports (typically up to four with only two interrupts), serial interface box 208 extends the number of serial devices that PC 202 can service. A suitable serial interface box 208 is the model CPM series of control port managers manufactured by Western Telematic, Inc. of Irvine, Calif. In an exemplary embodiment, serial interface box 202 used RS-232 protocol, but in certain application, other serial protocols may be suitable.

Serial interface box 208 includes one common port 208a coupled to a serial port of the PC 202 and a plurality of device ports 208b, with each one of the device ports 208b coupled to a sensor or monitoring device. In the exemplary and not limiting embodiment shown in FIG. 2, serial interface box 208 is coupled to serial devices such as environmental sensors 204, biosensors 206, environmental control system 210, patient monitoring unit 214, medication dispensing unit 212, door sensor 220, window sensor 222, motion detector 224, and non-motion detector 240. In this manner, the serial interface box 208 multiplexes several serial devices onto the serial communication link coupling PC 202 to serial interface box 208.

PC 202 controls serial interface box 208 and directs it to connect one of the multiplexed serial devices to the serial port of PC 202. In an exemplary embodiment, serial interface box 208 maintains a look-up table mapping each device ports 208b to a given multiplexed serial device. When the serial device coupled to a given device port 208b generates an interrupt, serial interface box 208 looks up the interrupting device port 208b in the table, and generates an appropriate interrupt to PC 202.

As discussed above, serial interface box 208 may be coupled to one or more of a plurality of multiplexed serial devices, including biosensors 206, environmental sensors 204, environmental control system 210, patient monitoring system 214, door sensor 220, window sensor 222, motion detector 224, and non-motion detector 240. Biosensors 206 and environmental sensors 204 are illustrated and discussed in more detail below in FIG. 7. Environmental control system 210 is illustrated and discussed in more detail below in FIG. 3.

Door sensor 220 detects the opening and closing of any doors leading to the patient's room. By tracking when the open/close status of the doors, door sensor 220 can assist in locating the patient and can detect when other persons have entered the patient's room. Similarly, window sensor 222 detects the opening and closing of any windows in a patient's room.

Motion detector 224 provides a signal indicating movement within the patient's room. Suitable motion detectors are commercially available and typically operate using infrared beams or sound waves. PC 202 monitors the signal from motion detector 224 to ensure that the patient is active. When there is no signal from motion detector 224 for some time interval, PC 202 concludes that the patient is inactive and possibly in danger, and issues appropriate alerts to central station 100. Conversely, where it is preferable to detect when there has been no motion in the room over some time interval, a non-motion detector 240 can be coupled to serial interface box 208. Non-motion detector 240 signals when there has been no motion within the room over some time interval. Using one or both of these detectors, PC 202 can monitor whether the patient has not moved over a given time interval, and issue appropriate alerts as dictated by the patient's activity level and programmed into patient monitoring system 10.

Patient monitoring unit 214 is coupled to one of the device ports 208b provided by serial interface box 208 and communicates with the PC 202 through serial interface box 208. Patient monitoring unit 214 functions to monitor the vital signs of the patient located at remote site 200. When the vital signs of the patient fall outside certain thresholds, possibly indicating that the patient is in discomfort, in danger, or in need of attention, patient monitoring unit 214 generates a nurse-call signal on line 214a. The nurse-call signal alerts medical support personnel that the patient demands immediate attention. Also, patient monitoring unit 214 supplies raw signals representing the patient's vital signs to PC 202 via serial interface box 208. PC 202 processes these signals to determine the status of the patient independently of patient monitoring unit 214. In this manner, PC 202 provides redundant monitoring of the patient, so that if patient monitoring unit 214 or PC 202 fails, the other provides back-up patient monitoring.

A suitable patient monitoring unit 214 is the Welch-Allyn LifeSign™ unit. The LifeSign™ unit measures the patient's blood pressure and pulse rate, and provides programmable alarms for high and low systolic and diastolic blood pressure and pulse rate. The LifeSign™ unit provides both visual and audio alarms, and stores monitoring data in memory and on hardcopy. The LifeSign™ unit also allows programming of the pressure to which the blood pressure cuff's is inflated, and monitors pulse oximetry as well.

Security system 226 may be coupled to PC 202, to serial interface box 208, and to patient monitoring unit 214. Security system 226 is also coupled directly to is central station 100 by a dedicated alert link 226a. Using this dedicated alert link 226a, security system 226 can bypass PC 202 and alert central station 100 directly. Security system 226 is coupled to receive the nurse-call signal on line 214a, and can alert central station 100 in response to the nurse-call signal. Security system 226 is coupled to alert PC 202 when it receives the nurse-call signal on line 214a. This dual-notification structure between PC 202 and security system 226 provides separate redundant paths by which to notify central station 100 when the patient needs attention. If security system 226 or dedicated alert link 226a between security system 226 and central station 100 fails, the link between PC 202 and central station 100 provides a back-up communication link. Conversely, if the link between PC 202 and central station 100 fails, then dedicated alert link 226a between security system 226 and central station 100 provides a back-up communication link.

Security system 226 functions generally to monitor the status of the patient and the patient's environment, and to generate alert signals when necessary. A suitable security system 226 is one of the ESPIRIT line of control panels manufactured by Paradox Security Systems, Inc. The ESPIRIT line of control panels provides integrated keypads for the entry of security codes, and these control panels are configured to monitor a plurality of security zones.

Security system 226 is coupled to a plurality of subcomponents, including a battery backup system 228, a heat sensor 230, an emergency pendant 238, a display 234, and a keypad 232. Battery backup system 228 provides an alternate power supply should the primary AC power supply at the remote site 200 fail.

Heat sensor 230 monitors the ambient temperature of the patient's room and generates appropriate alerts when the ambient temperature is either too high or too low. A suitable heat sensor 230 is the Intellitemp T-1000 manufactured by Intellisense™ Systems, Inc. of Louisville, Ky.

Emergency pendant 238 is adapted for carrying by the patient, and is coupled to the security system 226 by a direct wire or a wireless communication link. When the patient requires immediate assistance and cannot speak or otherwise signal his or her distress, the patient presses a button on emergency pendant 238 to notify security system 226 (and ultimately central station 100) of his or her distress. The Linear Corporation of Vista, Calif. provides a DXR-701 digital receiver, along with a hand-held transmitter unit compatible with the DXR-701. The hand-held transmitter unit can provide a suitable emergency pendant 238, if the DXR-701 digital receiver is coupled to the security system 226.

Garment 216 is adapted to house at least one patient sensor 218, and patient sensor 218 is coupled through a connector 215 to patient monitoring unit 214. The physical structure of garment 216 is illustrated and described below with respect to FIG. 6.

Medication dispensing unit 212 communicates with serial interface box 208 to receive commands from PC 202, and to transfer signals representing the status of medication doses to PC 202. Medication dispensing unit 212 is described in more detail below with respect to FIGS. 8–15 below. It should also be understood that in an alternate embodiment of the invention, medication dispensing unit 212 can function as a stand-alone unit separate from remote patient monitoring system 10.

In an exemplary embodiment, system 10 provides a video link 408 between central station 100 and each remote site 200 where it is necessary or desirable to have video communication with a remote site 200. Video link 408 allows patients to observe medical personnel demonstrate use of medical devices or diagnostic equipment. In addition, the medical personnel can directly observe the patients to ensure that they properly take medication, that they are in generally good or bad condition, that they are coherent, among other observations.

Visual communication device or means 300*a*, such as a VIA-TV phone, is provided at remote site 200 with a corresponding visual communication device 300*b* at central station 100. In an exemplary embodiment, visual communication devices 300 are transceivers capable of transmitting and receiving both image and audio signals. Visual communication device 300*a* is connected to central station 100 by video link 408, over which video and/or image data is exchanged. Video link 408 may include both dedicated and multiplexed communication lines, which are implemented with the same technologies discussed above with respect to communication links 400. It should be understood that if multiple remote sites 200 are equipped with visual communication devices 300*a*, then the visual communication device 300*b* located at central station 100 is coupled to each of the visual communication devices 300*a* that are provided at remote sites 200.

Figure 3:
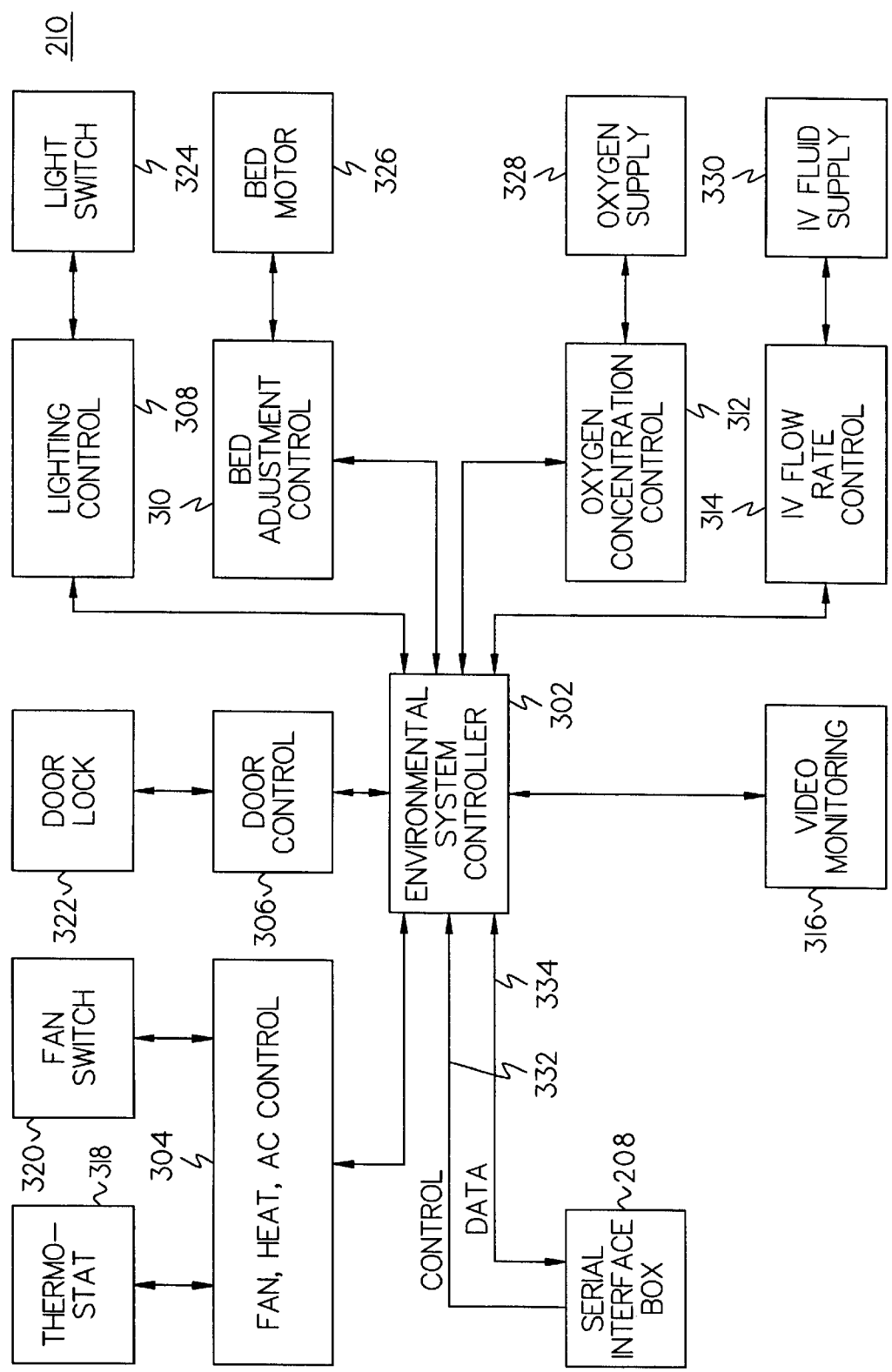
FIG. 3 is a diagram illustrating the various components of the environmental control system illustrated in FIG. 2.

FIG. 3 is a block diagram illustrating the various components of environmental control system 210 illustrated in FIG. 2. As shown in FIG. 3, environmental control system 210 interfaces with serial interface box 208 over a control line 332 and a bi-directional data line 334. Environmental control system 210 generally includes several control devices, such as an environmental system controller 302, a climate control 304, a door control 306, a lighting control 308, a bed adjustment control 310, an oxygen concentration control 312, an IV flow rate control 314, and a video monitoring unit 316. Environmental system controller 302 is typically a microcontroller programmed to interact with serial interface box 208, and to control each of the control devices shown in FIG. 3, according to instructions received through serial interface box 208. Climate control 304 adjusts the heating, cooling and ventilation within the patient's room. As such, climate control 304 may control the operation of ventilation systems in the room including ceiling fans, ceiling ventilators, or window ventilators in order to enhance the patient's comfort. Climate control 304 also interfaces with the heating, ventilation, air conditioning (HVAC) thermostat system within the room to regulate the temperature in the room as necessary. In this manner, the climate within the patient's room can be controlled remotely through the environmental control center 210 by passing commands through serial interface box 208.

Door control 306 regulates access to the patient's room. According to one aspect of the invention, the doors leading into the patient's room are equipped with electromagnetic or other door locks 322 that are operable by door control 306. Door control 306 responds to commands from environmental system controller 306 engage door lock 322. In this manner, personnel at central station 100 can regulate access to the patient's room by activating or deactivating door control 306, thereby enhancing patient security by controlling door lock 322. Door control 306 may be most suitable for a hospital or nursing home setting.

Lighting control 308 interfaces with environmental system controller 302, and controls at least one light switch 324 to adjust the level of lighting within the patient's room. In this matter, personnel in central station 100 can regulate the level of lighting in the room, turning on certain lights and turning off others as necessary to observe the patient or to enhance the patient's comfort. Light switch 324 can be an on-off switch or a dimmer switch. Lighting control 308 may be most suitable for a hospital or nursing home setting.

Bed adjustment control 310 interfaces with environmental system controller 302 to control the position and configuration of the patient's bed. As understood by those skilled in the art, hospital beds are often provided with electrically operated motors 326 that configure different portions of the bed, depending on the patient's comfort level and medical necessity. Bed adjustment control 310 provides an interface to these motors 326 and enables environmental system controller 302 to regulate the position of the bed. In this matter, personnel at central station 100 can adjust the bed remotely to enhance patient comfort and to promote recovery. Bed adjustment control 310 may be most suitable for a hospital or nursing home setting.

Oxygen concentration control 312 interfaces with environmental system controller 302 to control the level of oxygen in the patient's room by regulating oxygen supply 328. Oxygen concentration control 312 includes a sensor that indicates the level of oxygen within the room, and communicates that information to central station 100 through environmental system controller 302 and serial interface box 208. Certain patients, especially recovering pulmonary and respiratory patients, may require enhanced levels of oxygen in their environment during recovery and rehabilitation. For such patients, it may be necessary to provide supplemental oxygen through a nasal cannula if the oxygen level in the ambient air is insufficient. Oxygen concentration control unit 312 is coupled to such a nasal cannula and regulates the oxygen level provided in the nasal cannula.

IV flow rate control 314 interfaces with environmental system controller 302, and controls IV fluid supply 330 to adjust the rate of flow of IV fluids. In this manner, personnel at the central station 100 can remotely control the flow rate of IV fluids to the patient.

In an additional embodiment of the invention, a video monitoring unit 316 is provided to interface with environmental system controller 302, thereby providing a video link between the patient's room and central station 100. This video link is especially useful to facilitate visual contact and interaction between the support staff and the patient.

Figures 4, 4A:
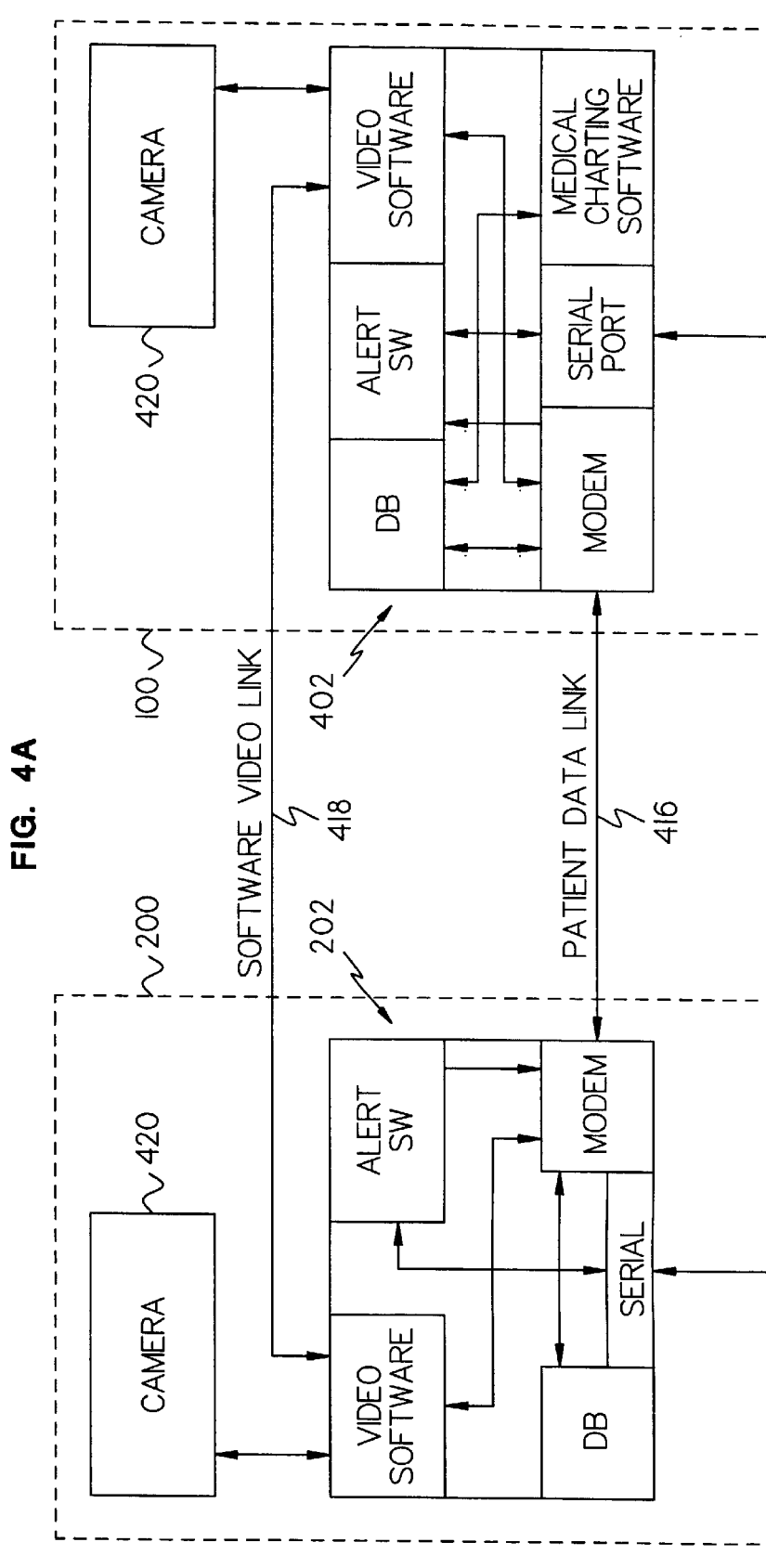
FIG. 4 is a diagram illustrating how the central station and the remote site are coupled to exchange data.
Figure 4B:
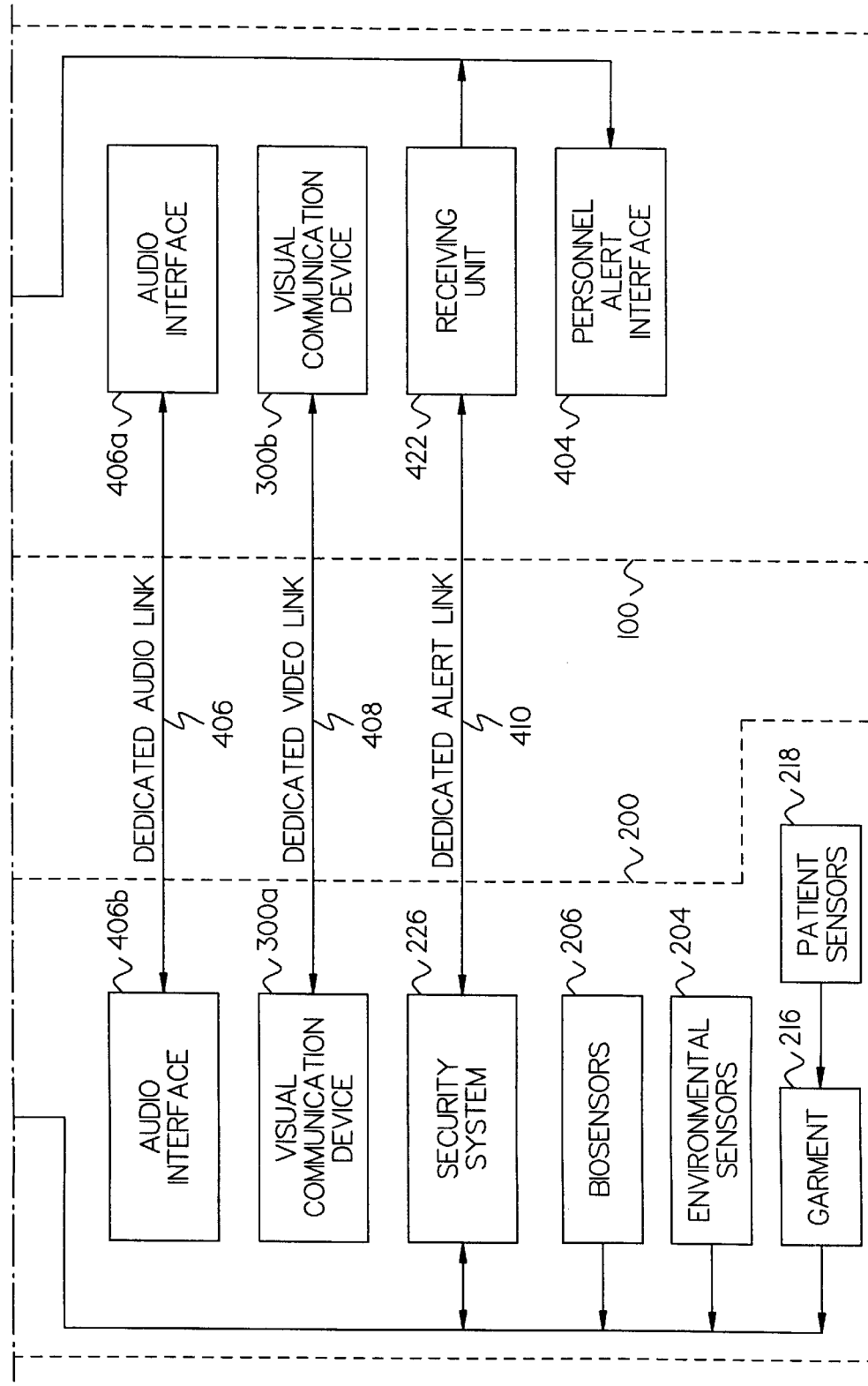

FIG. 4 is a diagram illustrating how central station 100 and remote site 200 are coupled to exchange data. The components of central station 100 shown in FIG. 4 are central server 402, personnel alert interface 404, audio interface 406a and visual communication device 300b. The components of remote site 200 shown in FIG. 4 are PC 202, security system 226, audio interface 406b, and visual communication device 300a.

Visual communication devices 300a and 300b are linked by a dedicated video link 408, which allows the two interfaces to communicate directly. In this manner, nursing personnel at central station 100 can directly monitor the patient at remote monitoring site 200 via video link 408. A suitable system for implementing visual communication devices 300a, 300b, and video link 408 is the VIA TV phone model 1905, manufactured by 8x8, Inc. of Santa Clara, Calif.

Audio link 406 links audio interfaces 408a and 408b, allowing audio communication between central station 100 and remote monitoring site 200. Dedicated audio link 406 provides another redundant level of communication between central station 100 and remote monitoring site 200.

In additional embodiments of the invention, personnel alert interface 404 is a speaker, a computer monitor capable of displaying suitable messages, a buzzer, or other communication interfaces.

The remote patient monitoring system enhances patient monitoring by providing redundant alert links between remote site 200 and central station 100. At remote site 200, security system 226 and PC 202 are coupled to personnel alert interface 404 at central station 100 by two redundant alert links. Dedicated alert link 410 links security system 226 directly to personnel alert interface 404, while software alert link 414 connects PC 202 to the personnel alert interface 404. Furthermore, security system 226 is linked to PC 202 by cross-link 412.

Security system 226 and PC 202 each independently monitor the status of the patient's vital signs at remote site 200 using separate sets of sensors. When PC 202 senses data indicating that the patient requires urgent attention, it generates an alert signal along software alert link 414 to personnel alert interface 404 at central station 100. PC 202 also generates a signal on cross-link 412 to security system 226, causing security system 226 to generate an alert signal on dedicated alert link 410 to personnel alert interface 404.

Using two redundant alert links, remote site 200 provides two alert signals to central station 100, one along software alert link 414 and another along dedicated alert link 410. Should one of the links fail, the other link serves as a back-up, thereby insuring that the personnel at central station 100 are notified of the urgency to attend to the patient at remote site 200. Likewise, should security system 226 detect that the patient needs urgent attention, it can generate an alert signal along its dedicated alert link 410, and can also generate appropriate alert signals along cross-link 412 to PC 202. PC 202 can then generate a redundant alert signal along its software alert link 414, thereby providing two alert signals to the personnel at central station 100.

In an exemplary embodiment, PC 202 is equipped with video software 202a, alert generation software 202b, database 202c, and communication port 202d. At central station 100, central server 402 is equipped with video software 402a, which is linked to video software 202a on PC 202 via software video link 418. Suitable video software is the ProShare product from Intel Corporation.

Central server 402 is also equipped with medical charting software 402b, database 402c, and a receiver unit 402d. Communication port 202d is linked to receiver unit 402d by a patient data link 416. Medical charting software 402b receives data from database 402c.

Suitable receiver units 402d are the SG-SLR single-line digital receiver and the MLR2-DG multi-line digital receiver, both manufactured by Sur-Gard Security Systems LTD of Montreal, Canada.

Figure 5:
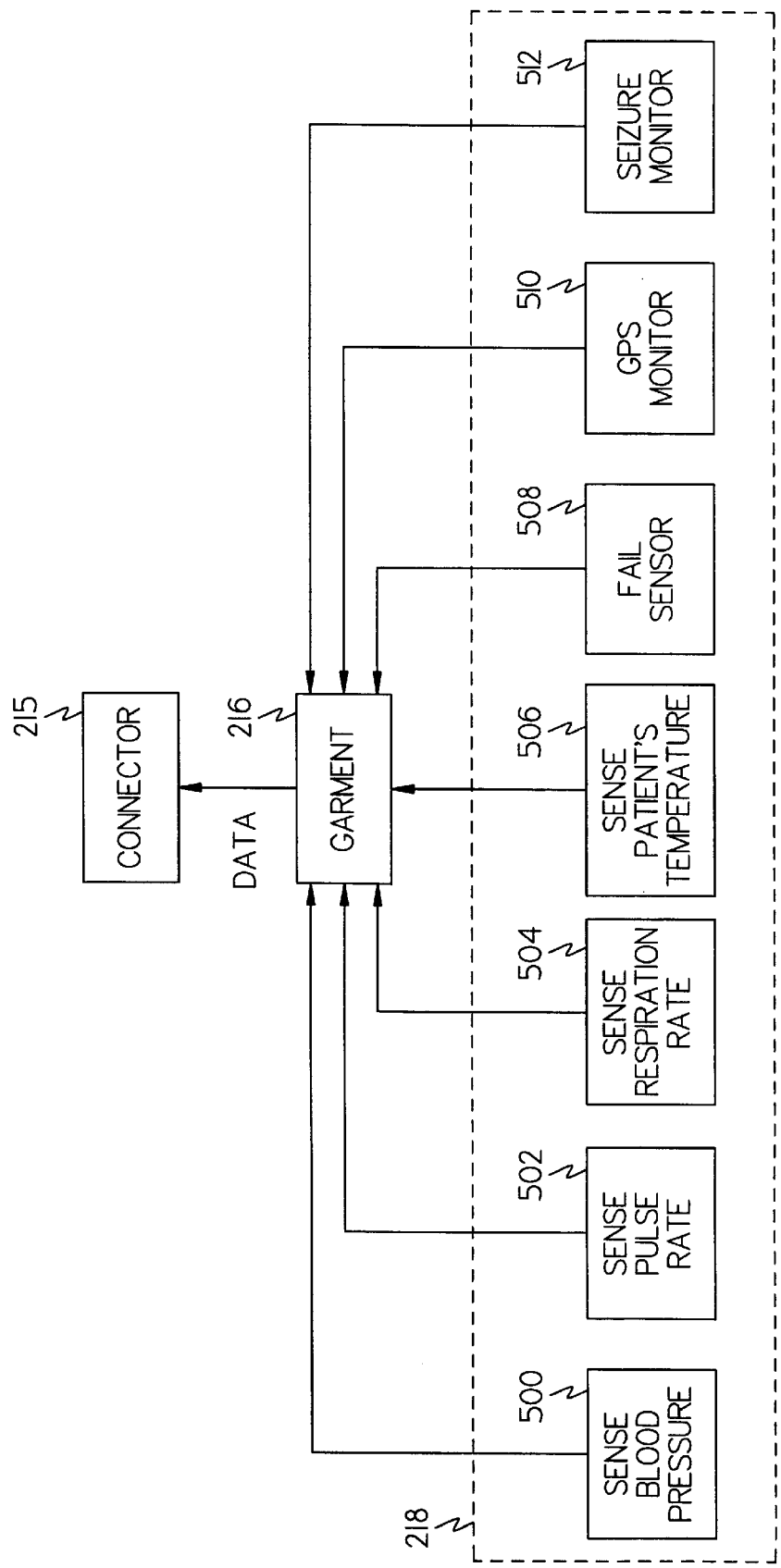
FIG. 5 is a diagram of the several patient sensors coupled to the garment shown in FIG. 2.

FIG. 5 is a diagram of the several patient sensors 218 coupled to garment 216, as shown in FIG. 2. FIG. 5 illustrates several exemplary sensors that can be provided as patient sensors 218. In the exemplary and not limiting embodiment shown in FIG. 5, patient sensors 218 refer collectively to blood pressure sensor 500, pulse rate sensor 502, respiration rate sensor 504, body temperature sensor 506, position sensor 508, GPS monitor 510, and seizure monitor 512. It should be understood that at least one sensor is housed in garment 216, with the number and type of sensors chosen as appropriate for a given application.

Several examples of optional sensors 218 are now discussed separately. Sensor 500 senses the patient's blood pressure, and may be a blood pressure cuff or other suitable device for measuring blood pressure. Sensor 502 monitors the patient's pulse rate. Sensor 504 monitors the patient's rate of respiration. Sensor 506 monitors the patient's body temperature. Sensor 508 monitors the patient's position and indicates if the patient has fallen. Sensor 510 is a monitor that interacts with a global positioning system (GPS). GPS monitor 510 can be used to track the patients whereabouts with precision and to locate and direct a lost or disoriented patient. Seizure monitor 512 senses whether the patient is having any type of a seizure, for example by monitoring the brain activity of the patient.

Figure 6:
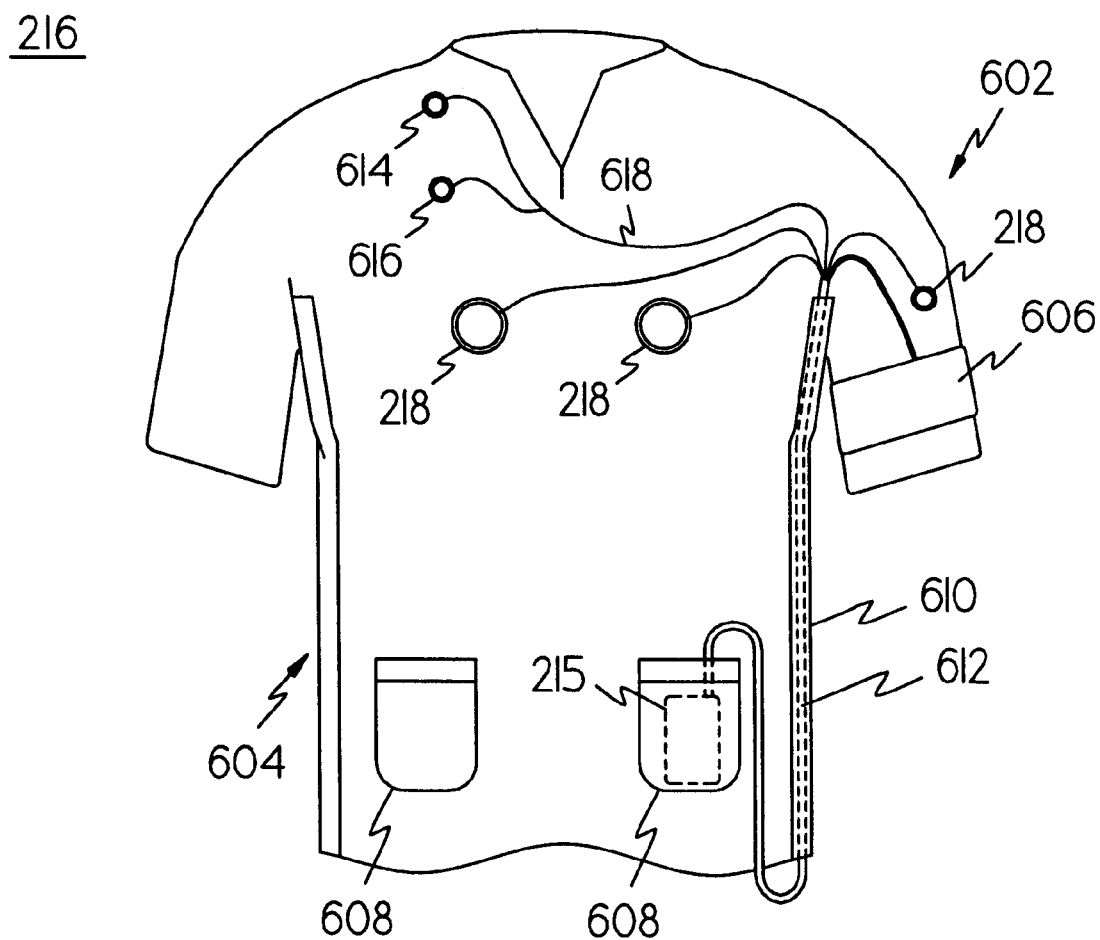
FIG. 6 is a diagram of an exemplary garment in accordance with the present invention.

FIG. 6 is a diagram of an exemplary garment 216 in accordance with the present invention. Garment 216 is adapted to house at least one sensor 218, and sensor 218 is coupled to the connector 215. Connector 215 provides a medium through which the sensor 218 communicates with patient monitoring unit 214. Garment 216 includes a sleeve portion 602 adapted to fit the patient's upper arm, and a torso portion 604 adapted to fit the patient's upper body. Sleeve portion 602 includes a pouch 606 adapted to receive a blood pressure cuff (not shown) to monitor the patient's blood pressure.

Garment 216 promotes remote patient monitoring by allowing the patient to properly locate sensor 218 by putting on garment 216 and wearing it. Once garment 216 is sized to fit a given patient, and is fitted appropriately with sensor 218, the patient can wear garment 216 and simultaneously locate sensor 218 properly. In additional embodiments, garment 216 can be fitted with a plurality of sensors 218 to monitor various patient vital signs, depending on the patient's medical condition. Once garment 216 is equipped with sensor 218 and fitted to a given patient, medical support personnel no longer need to travel to the remote site 200 to position sensor 218 on the patient's body.

Torso portion 604 and/or sleeve portion 602 define a channel 610 linking connector 215 to each of the sensors 218. Garment 216 promotes remote patient monitoring by allowing the patient to properly locate the sensors on the patient's torso. Channel 610 houses a signal transmission conduit 612 that couples each of sensors 218 to connector 215. Depending on the requirements of a given application, signal transmission conduit 612 may be an electrical conductor or a blood pressure tube coupled to the blood pressure cuff housed in pouch 606.

Depending on the patient monitoring designated for a particular patient, sensors 218 housed in garment 216 can be bio-sensors, including but not limited to EKG sensors, spirometers, and glucometers. Garment 216 is configured to place each sensor 218 in communication with the body of the patient, as required by the characteristics of a particular sensor 218.

Depending on the patient monitoring designated for a particular patient, garment 218 is equipped with a speaker 614, a microphone 616, and at least one conductor 618 coupling speaker 614 and microphone 616 to connector 215. It should be understood that FIG. 6 illustrates speaker 614, microphone 616, and sensor 218 in exemplary and not limiting positions. Using speaker 614 and microphone 616, central station 100 can communicate with the patient to long as the patient is wearing garment 218. If a wireless link exists between connector 215 and patient monitoring unit 214, then the patient is free to move away from patient monitoring unit 214 without losing contact with central station 100.

Patient monitoring unit 214 communicates with sensor 218 through connector 215, and is configured to transmit signals from sensor 218 to PC 202 for recording. In an exemplary embodiment, connector 215 is physically connected to patient monitoring unit 214. Alternatively, connector 215 can communicate with patient monitoring unit 214 through an RF or other wireless, electromagnetic link. With either embodiment, the patient is free to selectively disconnect connector 215 from patient monitoring unit 214. In the former embodiment, data does not flow between the sensor 218 and the patient monitoring unit 214 until the connection is re-made, but with the latter embodiment, data can flow at all times.

Connector 215 promotes remote patient monitoring by providing a quick-connect, quick-disconnect means allowing the patient freedom of movement while still allowing central station 100 to monitor the patient's vital signs. Connector 215 is described in more detail in connection with FIG. 21 below.

Typically, patient monitoring unit 214 is located at the patient's bedside. Patient monitoring unit 214 is also configured to exchange signals representing patient status with central station 100, where nursing or other hospital personnel are located.

Figure 7:
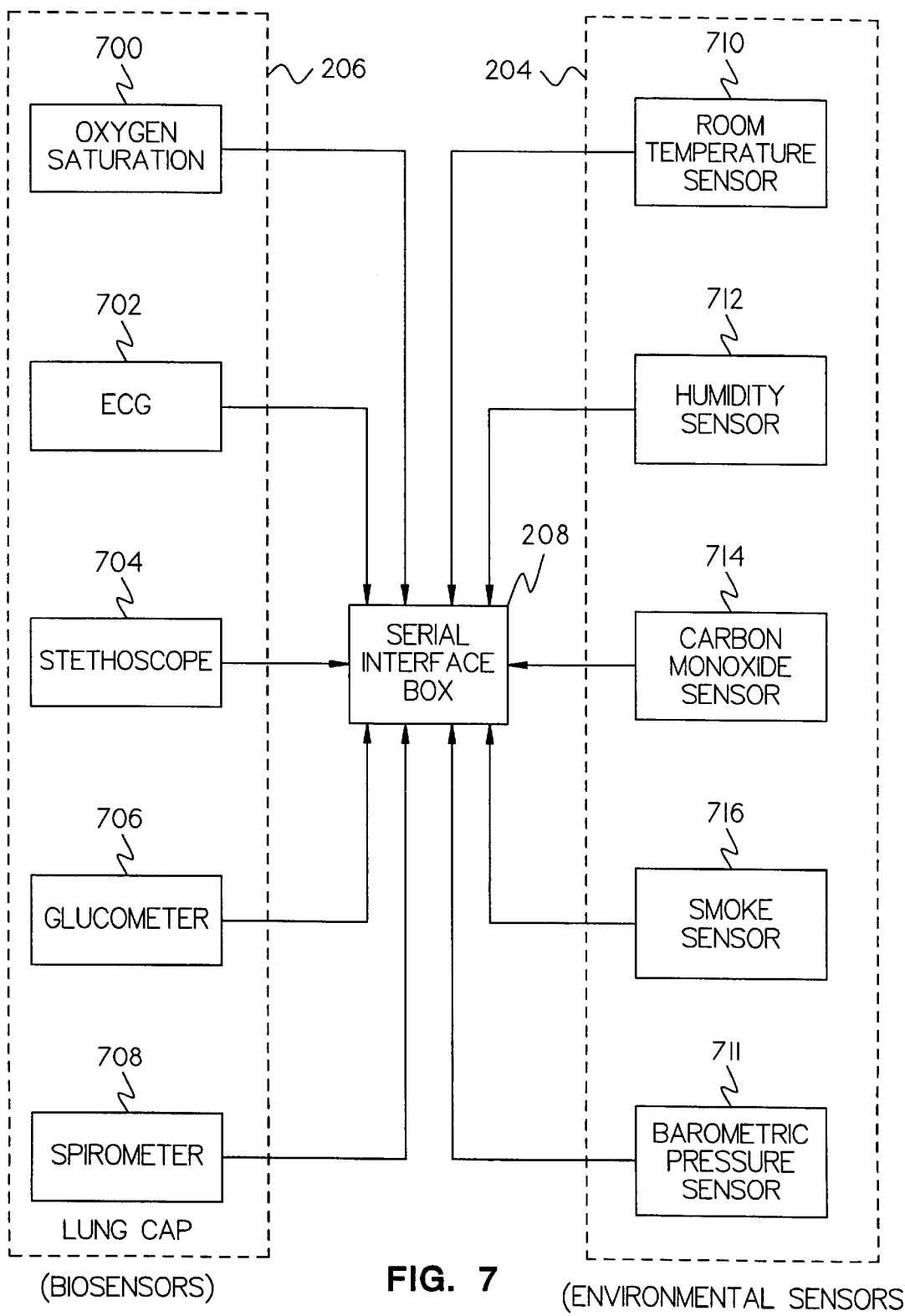
FIG. 7 is a diagram of several exemplary sensors that comprise the biosensors and the environmental sensors as shown in FIG. 2.

FIG. 7 is a diagram of several exemplary sensors that comprise biosensors 206 and environmental sensors 204 as shown in FIG. 2. Biosensors 206 and environmental sensors 204 are coupled to communicate with remote site 200 through serial interface box 208. Biosensors 206 may include, but are not limited to oxygen saturation sensor 700 to measure to oxygen level in the patient's bloodstream, electrocardiogram (ECG) 702 to measure the patient's cardiac activity, stethoscope 704, glucometer 706, and spirometer 708. Each of these bio-sensors 206 are coupled to serial interface box 208 to enable them to communicate with the rest of the system, especially patient monitoring unit 214 and PC 202.

Environmental sensors 204 may include, but are not limited to room temperature sensor 710, barometric pressure sensor 711, humidity sensor 712, carbon monoxide sensor 714 and smoke sensor 716. Room temperature sensor 710 and humidity sensor 712 sense the ambient temperature and humidity, respectively, in the patients room. The Perception II® unit manufactured by Davis Instruments provides an indoor temperature, barometric pressure, and humidity sensor that is suitable as room temperature sensor 710, barometric pressure sensor 711, and humidity sensor 712. Davis Instruments also provides Weather Link® software to collect, organize, and export data representing the climate conditions within a patient's room. Carbon monoxide sensor 714 monitors the level of carbon monoxide accumulating in the patient's room and generates a suitable alarm should the carbon monoxide level become hazardous. Carbon monoxide sensor 714 also provides a signal through serial interface box 208 indicating the level of carbon monoxide in the room so that air quantity can be monitored at central station 100. Smoke sensor 716 is a smoke detector configured to generate an appropriate alarm should it detect smoke in the ambient air in the patient's room.

Figure 8:
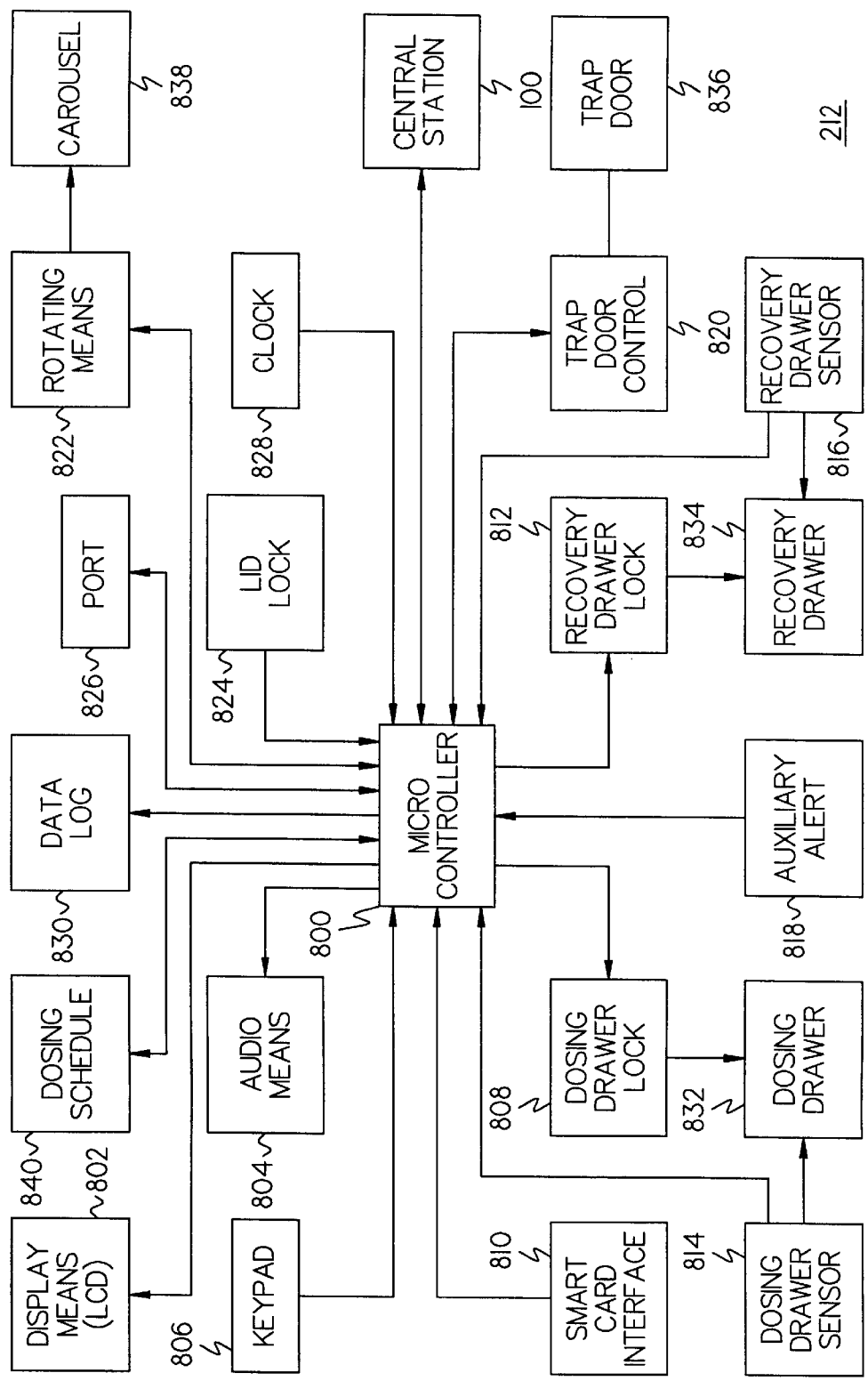
FIG. 8 is a block diagram of the various components of the medication dispensing unit shown in FIG. 2.

FIG. 8 is a block diagram of the various components of medication dispensing unit 212 shown in FIG. 2. The medication dispensing unit 212 includes a microcontroller 800 that interfaces with and controls the various components of an exemplary embodiment of medication dispensing unit 212, which components are described separately below.

Display means 802 include an LCD, LED, CRT, printer, or other suitable means for providing a visual readout to the user. Display means 802 is coupled to microcontroller 800 alert the patient to take a dose of medication and also to direct or instruct the patient how to take the dose of medication.

Audio means 804 includes a speaker and necessary support circuitry and is coupled to microcontroller 800 to alert the patient to take medication when the dosing interval arrives and also to provide verbal instructions on how to take the medication.

Display means 802 and audio means 804 play messages as commanded by microcontroller 800. These messages allow medication dispensing unit 212 to communicate with the patient by playing messages such as greetings, instructions, reminders, and alerts. Typically, a message is associated with an event, such as the beginning or ending of a dosing interval, the patient removing or replacing the dosing drawer, or a patient missing a dose of medication, and so on. The programming of medication dispensing unit 212 to associate messages with events, and the ability of medication dispensing unit 212 to support different languages, is described below in connection with FIGS. 25 and 26.

Keypad 806 is coupled to microcontroller 800 to allow healthcare workers to login or sign-in at remote site 200. Healthcare workers in this context refers to licensed personnel such as nurses or pharmacists if the medication is being dispensed from bulk. However, if the medication doses are pre-packaged and sealed, those doses may be handled and delivered by unlicensed personnel such as delivery couriers. Once they have logged in, the healthcare workers can use the keypad 806 to interact and communicate with the medication dispensing unit 212. Such workers can access data stored on the microcontroller 800 as necessary or can customize the operation and/or configuration of the microcontroller 800 for a particular environment.

Dosing drawer 832 contains a dose of medication to be administered during one dosing interval and keeps it accessible to the patient during the dosing interval. Microcontroller 800 determines whether dosing drawer 832 has been removed from medication dispensing unit 212 by monitoring dosing drawer sensor 814. Dosing drawer sensor 814 may be a micro-switch or other electrical contact that indicates when the patient has withdrawn and removed dosing drawer 832. Microcontroller 800 also controls a dosing drawer lock 808 that selectively locks dosing drawer 832 and prevents its withdrawal and removal by the patient until a dosing interval arrives. A suitable dosing drawer lock 808 employs a solenoid or similar electro mechanical mechanism.

Recovery drawer 834 stores doses of medication that are dropped from dosing drawer 832 when the patient fails to take the medication within the dosing interval. Microcontroller 800 monitors the status of recovery drawer sensor 816, which is a micro-switch or other electrical contact that indicates when recovery drawer 834 has been withdrawn and removed. Microcontroller 800 controls access to recovery drawer is 834 through recovery drawer lock 812. Generally, microcontroller 800 locks recovery drawer 834 through recovery drawer lock 812 to prevent any unauthorized access. If an authorized person such as a nurse or other support personnel enters the appropriate security code through keypad 806, however, microcontroller 800 releases recovery drawer lock 812 and allows recovery drawer 834 to be removed for inspection.

Carousel 838 contains a plurality of doses of medication and is rotated as necessary to drop successive doses of medication into dosing drawer 832. Rotating means 822 is coupled to selectively rotate carousel 838 under the control of microcontroller 800. Rotating means 822 is a suitable electric motor providing feedback such as a stepper motor or a servo motor, along with the necessary interface circuitry coupling the motor to microcontroller 800. It should be understood that carousel 838 is provided as an exemplary embodiment; other devices for storing and dispensing doses of medication are suitable as well.

Lid lock 824 is attached to the housing of medication dispensing unit 212, and is locked in place by microcontroller 800 to prevent unauthorized access to carousel 838. As with recovery drawer 834 discussed above, lid lock 824 can be released by microcontroller 800 if the appropriate security code is entered by authorized personnel through keypad 806.

Trap door 836 is provided to control communication between dosing drawer 832 and recovery drawer 834. According to various aspects of the present invention, trap door 836 is a separate component from dosing drawer 832 and recovery drawer 834, or is configured as part of a lower portion of dosing drawer 832. Trap door control 820 controls the operation of trap door 836 under the direction of microcontroller 800. As discussed in connection with the flowchart in FIG. 10 below, when a dosing interval expires without the patient accessing dosing drawer 832, microcontroller 800 activates trap door control 820 to open trap door 836. When trap door 836 is opened, the medication contained in dosing drawer 832 is dropped into recovery drawer 834. In an exemplary embodiment, when trap door control 820 is activated to operate trap door 836, microcontroller 800 is configured to activate an auxiliary alert 818 to notify the patient that a dosing interval has expired and that the patient has missed a dose.

It will be understood that microcontroller 800 synchronizes the operation of trapdoor 836 and the rotation of carousel 838, so that the next dose of medication is dropped into dosing drawer 832 after trap door 836 closes to cut communication with recovery drawer 834. In this manner, microcontroller 800 prevents the next dose of medication from being dropped directly into recovery drawer 834.

Although the exemplary embodiment discussed herein discloses trapdoor 836 communicating between dosing drawer 832 and recovery drawer 834, other alternative embodiments for preventing successive doses of medication from accumulating in dosing drawer 832 are within the scope of the invention. For example, various embodiments of trapdoor 836 are provided, with trapdoor 836 having sliding members or pivoting members.

In yet another embodiment, dosing drawer 832 and recovery drawer 834 can communicate in a side-to-side relationship, in addition to communicating in the upper-and-lower relationship discussed in the above exemplary embodiment. If dosing drawer 832 and recovery drawer 834 communicate in a side-to-side relationship, then a sweeping means may be provided to swipe the dose of medication from dosing drawer 832 into recovery drawer 834 when the patient misses a dose. A suitable sweeping means may be a blade or wiper adapted to fit the internal configuration of dosing drawer 832. This sweeping means can include a mechanical linkage under electronic or pneumatic control, but can also include a pneumatic system using compressed air or suction to transfer the dose of medication. In the upper-lower embodiment discussed above, a pneumatic system can also be used to assist the movement of the medication between dosing drawer 832 and recovery drawer 834.

In still further embodiments of the invention, dosing drawer 832 can be inverted to dump its contents into recovery drawer 834 if the patient missed a dose, thereby preventing double-dosing. Also, dosing drawer 832 can be configured to tip or otherwise release its contents into recovery drawer 834 through the sides, top, bottom, front, or back of dosing drawer 832.

In an additional embodiment, particularly where narcotics or other especially valuable drugs are dispensed in a home environment, recovery drawer 834 can be made more secure by recessing it laterally into housing 900 until the patient misses a dose. When the patient misses a dose, recovery drawer 834 can be pivoted about a vertical axis or slid laterally into position beneath dosing drawer 832. If this embodiment is chosen, housing 900 is provided with a recessed opening sized snugly to fit recovery drawer 834. This configuration promotes security by presenting only a side wall of recovery drawer 834 when recover drawer 834 is recessed into housing 900 and dosing drawer 832 is removed, rather than presenting trapdoor 836. Typically, a side wall of recover drawer 834 is more rugged and harder to defeat than trapdoor 836, because unlike trapdoor 836, the side wall has no moving parts. In this embodiment, the moving parts of trapdoor 836 are recessed into, and protected by, housing 900.

A communication port 826 is coupled to microcontroller 800. An exemplary communication port 826 is a serial port that allows data to be uploaded or downloaded from microcontroller 800 as necessary. Communication port 826 might be used, for example, to upload new software into microcontroller 800, to download data from microcontroller 800 reflecting taken or missed doses over a given time interval, or to upload a new medication dispensing schedule into microcontroller 800. Communication port 826 also allows support personnel to otherwise interact with microcontroller 800, such as with a portable laptop PC, and to connect medication dispensing unit 212 with PC 202.

Communication port 826 can be configured to support Internet transmission of data to and from medication dispensing unit 212. For example, if the patient misses a dose, medication dispensing unit 212 can be configured to broadcast an e-mail message to the pharmacist, medical support personnel, or to a physician. Also, medication dispensing unit 212 could be programmed via Internet communication, if appropriate security precautions are taken.

Clock 828 is coupled to microcontroller 800 to provide a real-time clock signal and to coordinate and synchronize tile various functions of microcontroller 800. Using signals from clock 828, microcontroller 800 keeps track of a dose schedule that specifies when dosing intervals begin and end. In this manner, microcontroller 800 tracks the beginning and ends of the dosing intervals using the real-time kept by clock 828.

Dosing schedule 840 defines how many dosing intervals occur over a given time, and when each of these dosing intervals begin and end. The structure of an exemplary dosing schedule 840 is discussed below in connection with FIG. 9.

Data log 830 is a record maintained by microcontroller 800 containing entries for successful doses and missed doses. This record is updated by microcontroller 800. Data log 830 can be accessed by authorized personnel through key pad 806 by entering an appropriate password or other security code. The structure of data log 830 is discussed below in connection with FIG. 10.

According to an exemplary embodiment, smart card interface 810 can be provided as a means for loading dose instructions to microcontroller 800. The term "smart card " in the context of this application refers to a credit-card sized device that is equipped with a microprocessor and memory and that is capable of transferring information to or from a central computer. A smart card can be built into carousel 838, and programmed by the pharmacist at the time that the carousel 838 is stocked with medication. At that time, the smart card 810 can be configured or programmed with the appropriate dose instructions in whatever language is appropriate for a given patient.

When the carousel 838 is loaded into the medication dispensing unit 212, the smart card interface 810 also loads the dose instructions from the carousel 838. In this manner, microcontroller 800 is updated with the appropriate instructions when a new carousel 838 is loaded. In additional embodiments, a magnetic strip reader can be used as an alternative to the smart card interface 810. In addition, dosing instructions may be loaded at remote site 200 through serial port 826. In an additional embodiment, dose instructions can be transmitted by central station 100 directly to microcontroller 800.

Figure 9:
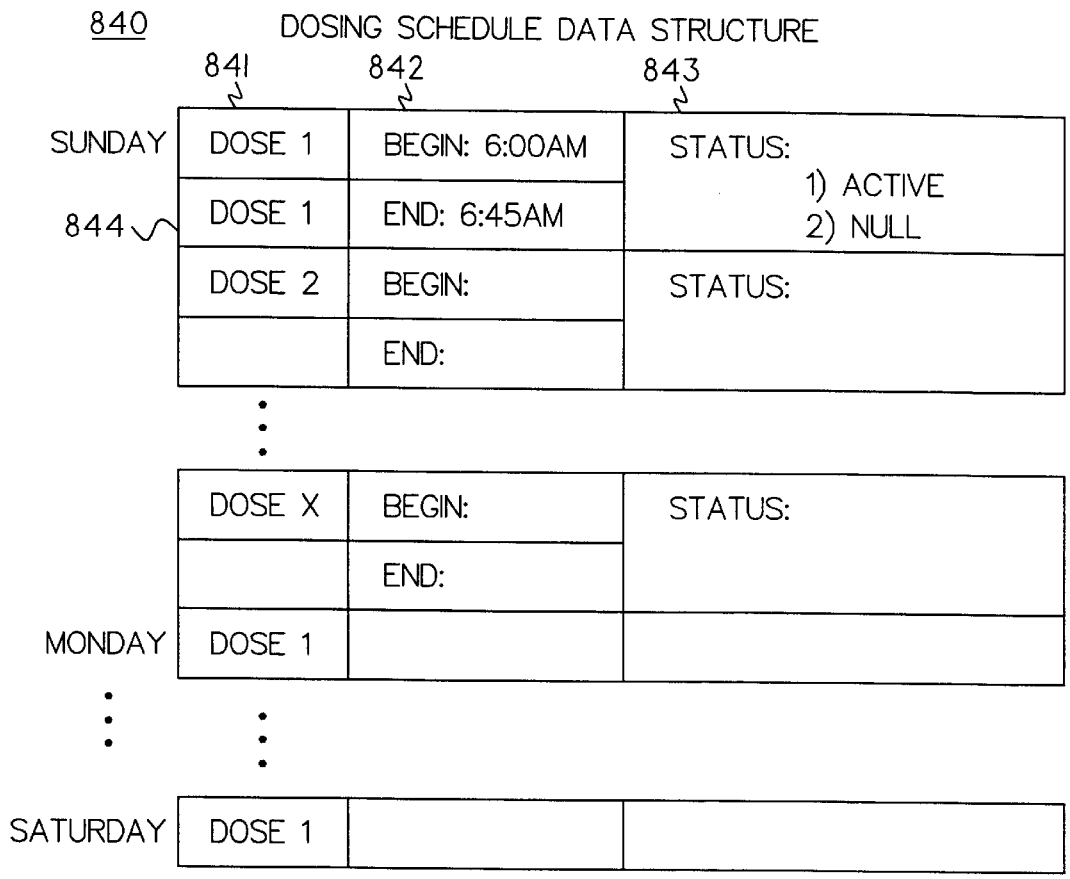
FIG. 9 illustrates an exemplary data structure for a dosing schedule illustrated in FIG. 8.

FIG. 9 illustrates an exemplary data structure for dosing schedule 840, as illustrated in FIG. 8. Dosing schedule 840 is arranged as a linked list or an array of a plurality of records. In an exemplary embodiment, at least one of these records is associated with each of the days of the week. For example, if 4 doses are to be administered during a given day, there would be four records appearing in dosing schedule 840 for that given day.

Referring to an exemplary row 844, FIG. 9 shows that each row contains at least 3 data fields, which are numbered 841, 842, and 843. First data field, 841, contains a sequence number for a given dose. This sequence number can be ordered within a given day or can be ordered within a given week as suitable for a given environment. Second data field, 842, specifies the beginning time and the ending time of a given dosing interval. Third data field, 843, contains a status flag, which indicates whether a dose should be administered during that dosing interval. The flag can be assigned one value to indicate that a dose should be administered, and a second value to indicate that the dose should be skipped. In this manner, the same number of dosing intervals can be defined uniformly for each day of the week, and the doses to be administered during a given day can be adjusted as necessary by modifying the status flag in third data field 843. Also, if the status flag in data field 843 is set to an inactive status for a given dosing interval, this signals microcontroller 800 that dosing drawer 832 will not be accessed during that dosing interval, and that microcontroller 800 should not log a missed dose for that dosing interval.

Figure 10:
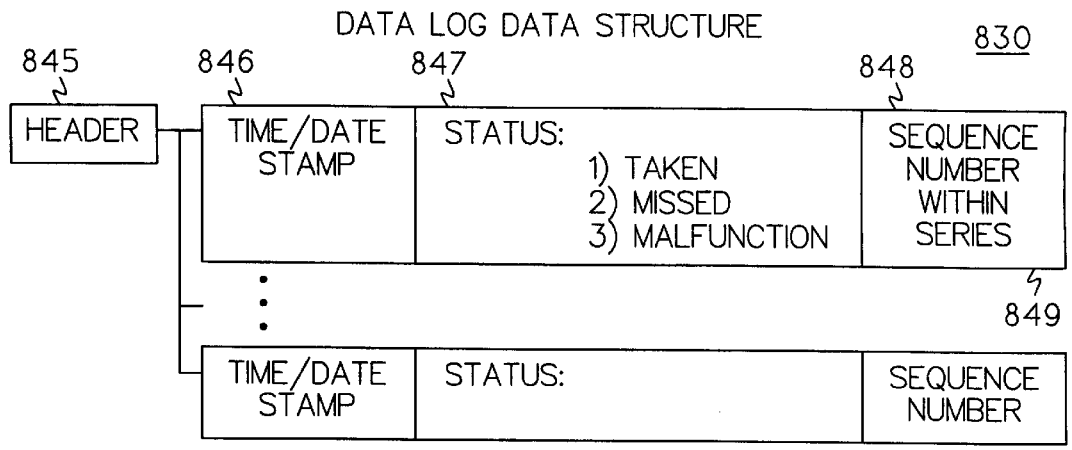
FIG. 10 illustrates an exemplary structure of the data log illustrated in FIG. 8.

FIG. 10 illustrates an exemplary structure of the data log 830 illustrated in FIG. 8. Data log 830 is arranged as a linked list or an array of a plurality of rows, such as an exemplary row 849. A header structure 845 contains pointer to each of the rows in data log 830. By referencing header 845, microcontroller 800 can readily search and locate any row in the data log 830, such as exemplary row 849.

Exemplary row 849 includes three sub-data fields: first data field 846, second data field 847, and third data field 848. First data field 846 stores a time and date stamp indicating the time at which the entry corresponding to that row is made in data log 830. Second data field 847 contains a status indicator that stores the status of the medication dose corresponding to a given row in data log 830. The status indicator can take on at least three values: a first value indicating that the dose was taken successfully, a second value indicating that the dose was missed, and a third value indicating that the medication dispensing unit 212 malfunctioned. Third data field 848 stores a unique identifier within a series of doses. For example, third data field 848 might indicate that a given dosing period was the first dose of a given day, a second dose in a given day, etc. By referring to data log 830, microcontroller 800 can determine when and if particular doses were missed by traversing data log 830 and selecting each record containing a second data field 847 having a status indicating a missed dose. Microcontroller 800 can also determine if there is a certain dose within a day that a patient chronically misses by searching for each missed dose and cataloging those missed doses.

Figure 11:
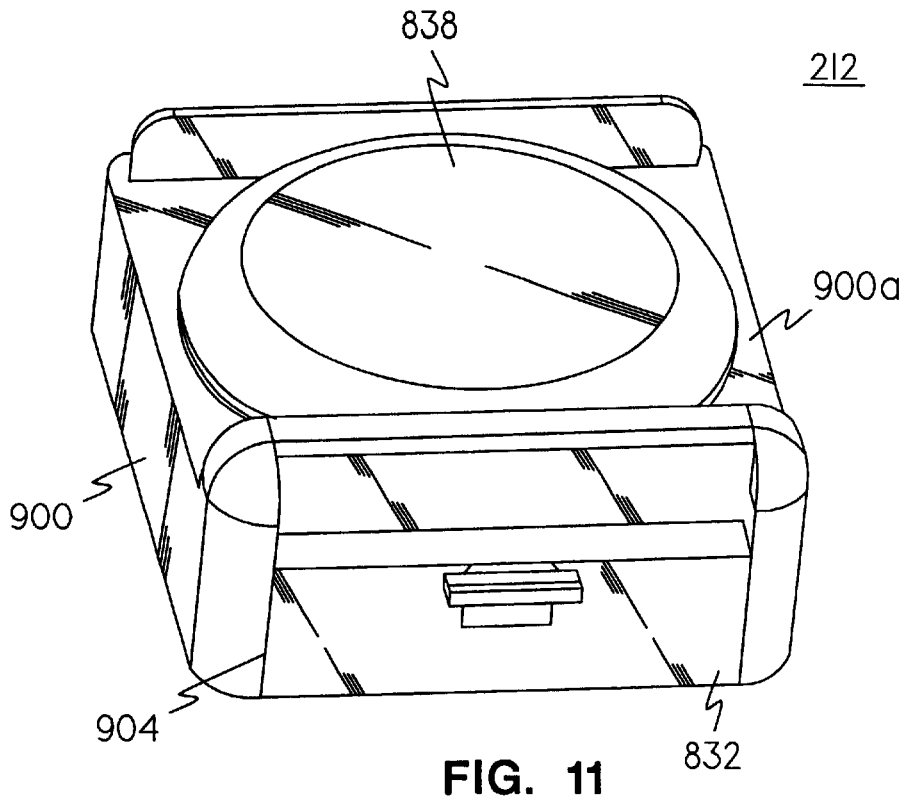
FIG. 11 is an elevated perspective view of the medication dispensing unit, shown from the front.

FIGS. 11–14 provide exemplary, and not limiting, views of the exterior of the medication dispensing unit 212. FIG. 11 is an elevated perspective view of the medication dispensing unit 212, shown from the front. FIG. 11 shows the medication dispensing unit 212 as assembled, and features carousel 838 positioned on medication dispensing unit 212 on the top of housing 900. Dosing drawer 832 is shown positioned in the front of housing 900.

Housing 900 includes a surface 900a adapted to receive carousel 838. Surface 900a is typically the top surface of housing 900. Housing 900 defines a receptacle 904 into which dosing drawer 832 is slidably positioned.

Figure 12:
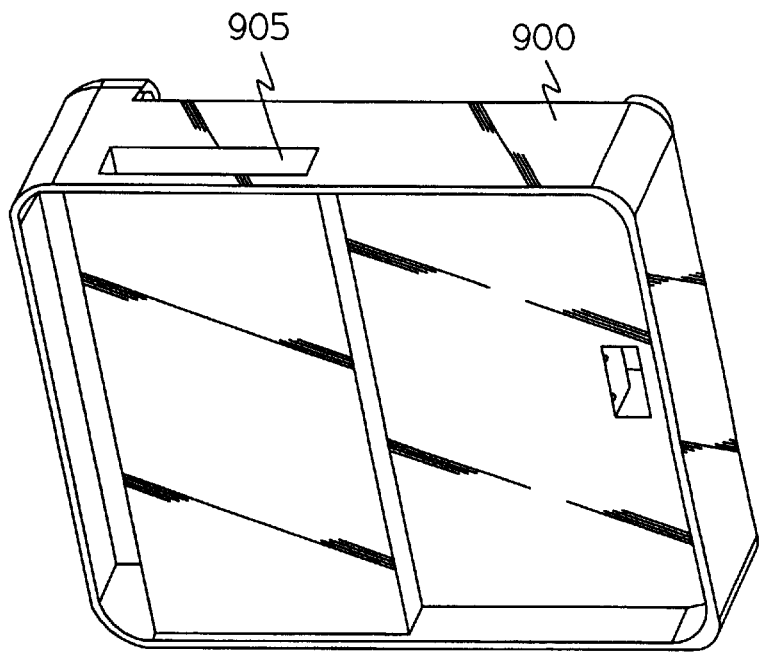
FIG. 12 is a perspective view of the bottom of the medication dispensing unit.

FIG. 12 is a perspective view of the bottom of medication dispensing unit 212, showing the opening 905, which receives recovery drawer 834. FIG. 9B shows medication dispensing unit 212 without recovery drawer 834 installed.

Figure 13:
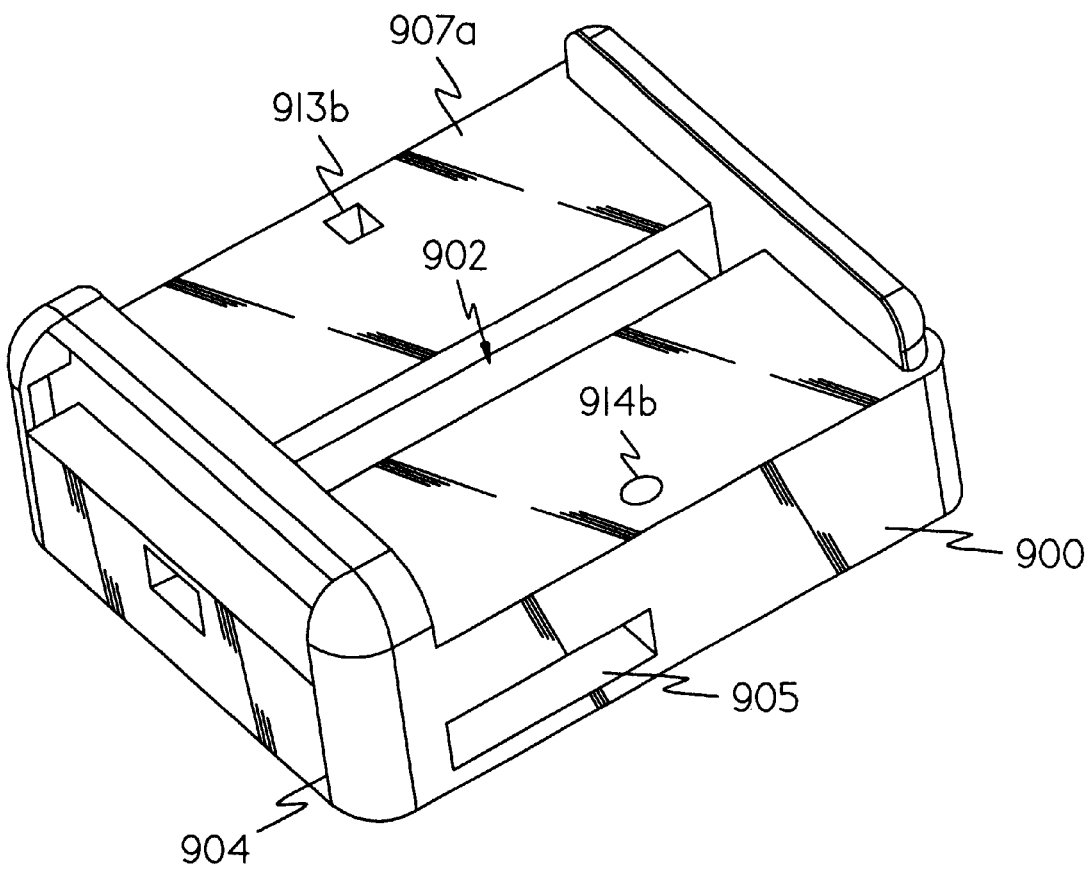
FIG. 13 is an elevated perspective view of medication dispensing unit, with carousel detached.

FIG. 13 is an elevated perspective view of medication dispensing unit 212, with carousel 838 detached. FIG. 13 also features opening 905 on the right side of housing 900. An access aperture 902 communicates between receptacle 904 and surface 900a adapted to receive carousel 838. Dosing drawer 832 is positionable within receptacle 904 and is in communication with access aperture 902.

Figure 14:
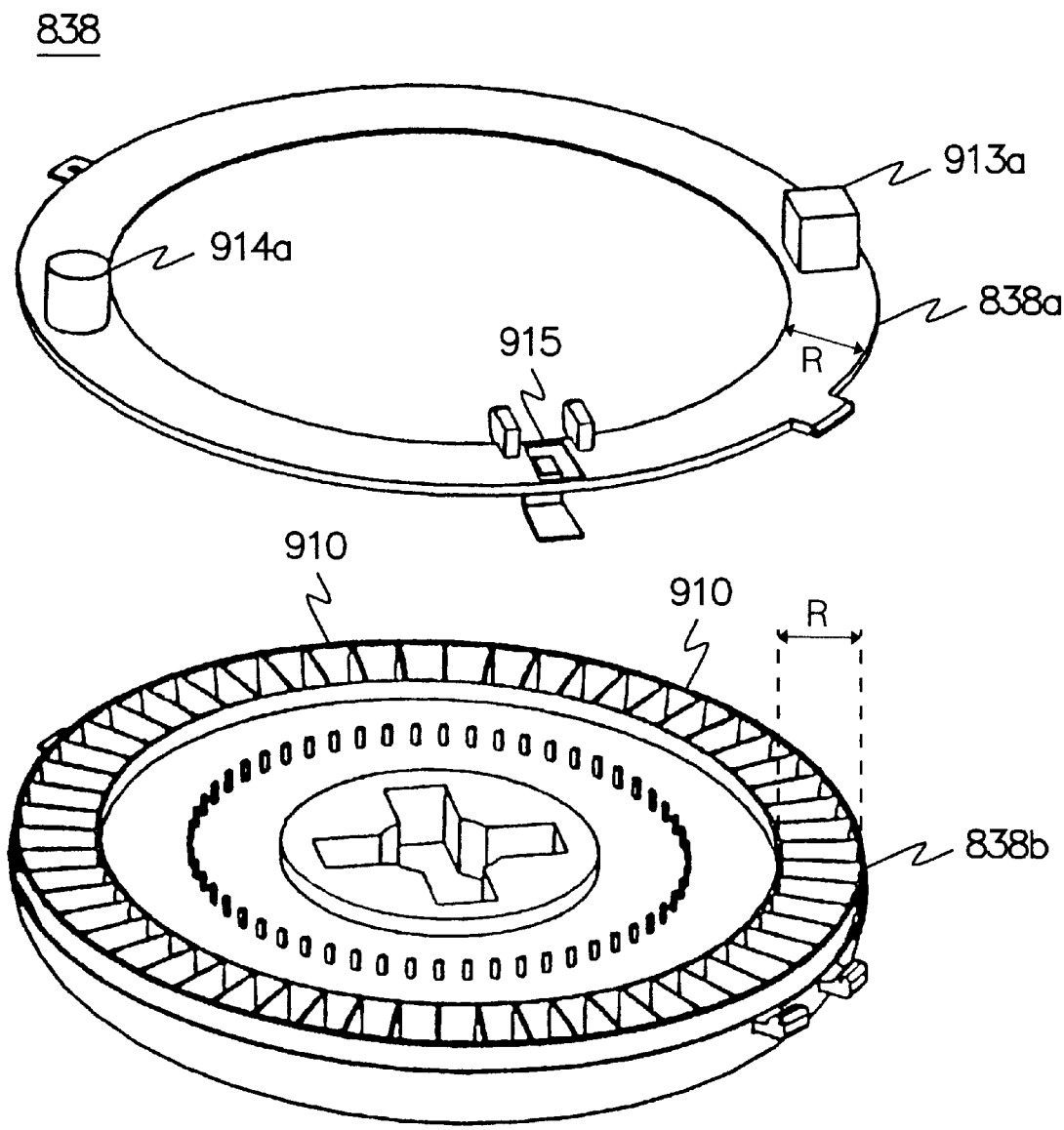
FIG. 14 is an exploded diagram of the carousel shown inverted.

FIG. 14 is an exploded diagram of carousel 838, which is shown inverted better to illustrate its essential features. Carousel 838 includes upper portion 838b and lower portion 838a. Upper portion 838b defines a plurality of compartments 910. Lower portion 838a snaps into upper portion 838b to trap the contents of compartments 910 within compartments 910. If carousel 838 is removed from housing 900, then the contents of compartments 910 can be accessed by removing lower portion 838a.

Lower portion 838a is an annular ring having approximately the same outside diameter as upper portion 838b. The radial thickness R of lower portion 838a is approximately the same as the radial length R of compartment 910. This feature allows lower portion 838b to maintain the medication in compartments 910.

Lower portion 838a is keyed to surface 900a of housing 900, such as by the exemplary keying means 913a and 914a, which engage complementary keying means 913b and 914b shown in FIG. 13. Thus, lower portion 838a is maintained stationary relative to housing 900. Conversely, upper portion 838b is free to rotate relative to housing 900 and lower portion 838a. Upper portion 838b includes keying means 916 that engage rotating means 822 (shown in block form in FIG. 8). Thus, rotating means 822 rotates upper portion 838b relative to housing 900 and lower portion 838a.

Lower portion 838a defines an aperture 915 that communicates with one compartment 910 when upper portion 838b and lower portion 838a are assembled. When carousel 838 is assembled and inverted, gravity pulls the contents, if any, of the one compartment 910 through aperture 915 and into access aperture 902. As rotating means 822 rotates upper portion 838b, successive compartments 910 are positioned above aperture 915 to drop their contents through aperture 915.

Access through aperture 915 is controlled by hinged member 915a. In one embodiment, hinged member 915a can be configured to open under control of microcontroller 800 when carousel 838 is loaded onto housing 900, and to remain open until carousel 838 is exhausted, typically after one month. However, in an additional embodiment, hinged member 915a can be configured to open and close as each compartment 910 is rotated into communication with aperture 915. For example, hinged member 915a can open when a first dosing interval arrives, thereby allowing the dose of medication to drop from compartment 910 into dosing drawer 832. If the patient fails to access that dose, however, hinged member 915a can be configured to close, thereby blocking subsequent doses from other compartments 910 from dropping into dosing drawer 832. After the missed dose is rectified, such as by alerting medical support personnel or a pharmacist, the hinged member 915a can re-open and resume operation so long as the patient does not miss any doses.

Once the medication exits carousel 838 through aperture 915, it drops into access aperture 902 defined by housing 900. A first one of the carousel compartments 910 is positioned to communicate with the receptacle 904 through the access aperture 902 defined by housing 900. Preferably, carousel 838 is positioned atop housing 900, with a first carousel compartment 910 above access aperture 902. In this manner, gravity causes the dose contained in the compartment to drop through access aperture 902 into dosing drawer 832. Preferably, access aperture 902 is a substantially vertical channel, thereby offering the advantage of allowing the medication to drop directly downwards without contacting the sides of access aperture 902. Thus, the medication does not contaminate, and is not contaminated by, the sides of access aperture 902.

In this manner, dosing drawer 832 receives the dose of medication from first carousel compartment 910 through access aperture 902. Preferably, dosing drawer 832 has an open top to allow the medication to drop in from access aperture 902. As described above, medication dispensing unit 212 is oriented so that gravity pulls the medication from first carousel compartment 910, through access aperture 902, and into dosing drawer 832.

Each compartment 910 is adapted to store a single dose of medication. Carousel 838 is pre-loaded with doses of medication to be administered over a given period, such as a week or a month. Carousel 838 is filled in bulk by a pharmacy, if the pharmacy is equipped to process carousels 838. Thus, the pharmacist segregates the medication into individual doses when filling the prescription, rather than having hospital workers administer individual doses to patients from medication supplied in bulk. This approach saves hospital labor costs and reduces the risk of error when administering individual doses.

According to different aspects of the present invention, carousel 838 is configured to electronically store dose instructions and schedules as encoded by the pharmacist. Further, carousel 838 transmits these electronic instructions to medication dispensing unit 212 when the carousel 838 is loaded onto housing 900.

Figure 15B:
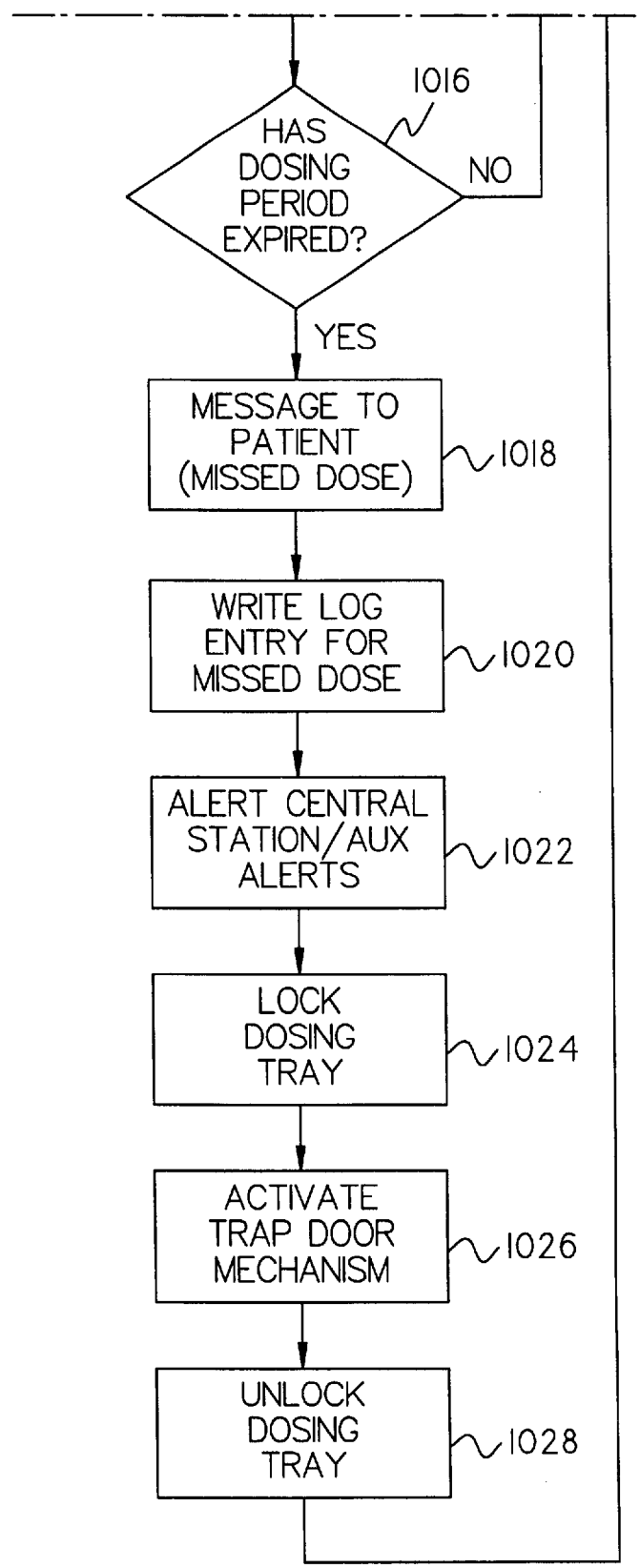
FIG. 15 is a flow chart illustrating the flow of processing performed by the microcontroller of the medication dispensing unit.

FIG. 15 is a flow chart illustrating the flow of processing performed by microcontroller 800 of medication dispensing unit 212. Processing starts at BEGIN block 1000.

At block 1002 microcontroller 800 evaluates whether a dosing period has begun. Microcontroller 800 is programmed with a dosing schedule, which defines at least one dosing interval. During this dosing interval, the patient is expected to retrieve the dose for that interval from medication dispensing unit 212. Until a dosing interval begins, microcontroller 800 loops back through block 1002, as indicated by the N branch.

Once the dosing interval has begun, as indicated by the Y branch from block 1002, microcontroller 800 proceeds to block 1004. At block 1004, microcontroller 800 engages rotating means 822 to rotate carousel 838 into position to drop a dose of medication into dosing drawer 832.

At block 1006, microcontroller 800 unlocks dosing drawer 832, if that drawer is locked for any reason. Thus, the patient is free to withdraw dosing drawer 832 to access the medication.

At block 1008, microcontroller 800 causes an audio alert to be sent to the patient, such as by beeps, whistles, or other audio alerts. These audio alerts should be chosen to attract the patient's attention and to remind him or her to take the medication.

At block 1010, microcontroller 800 causes visual alerts to be sent to the patient such as by blinking lights, blinking LEDS or other visual alerts, once again to attract the patient's attention.

At block 1012, microcontroller 800 provides dose directions to the patient. Such dose directions may include instructions on whether to take the medication on a full or empty stomach, with or without liquid, etc. These directions may also specify how many pills should be in dosing drawer 832, so that the patient can verify that the dose dropped into dosing drawer 832 is correct. These dose directions may be communicated to the patient over audio means 804 and/or visual means 802.

At block 1014, microcontroller 800 evaluates whether the patient has removed dosing drawer 832 from housing 900 of medication dispensing unit 212. When microcontroller 800 senses that the patient has removed dosing drawer 832, as indicated by the Y branch from block 1014, microcontroller 800 proceeds to block 1030. So long as the patient has not removed dosing drawer 832, and so long as the dosing interval has not expired, microcontroller 800 loops between blocks 1014 and blocks 1016. Microcontroller 800 detects when the patient has removed dosing drawer 832 by monitoring dosing drawer sensor 814.

At block 1030, microcontroller 800 evaluates whether the patient has replaced dosing drawer 832 into housing 900 of medication dispensing unit 212. When microcontroller 800 senses that the patient has replaced dosing drawer 832, microcontroller 800 proceeds by the Y branch to block 1032. So long as the patient has not replaced dosing drawer 832, microcontroller 800 loops via the N branch through blocks 1034 and 1036 and back to block 1030.

At block 1032, the patient has accessed the dose and has replaced dosing drawer 832. Microcontroller 800 then writes a log entry for the dose taken by the patient. Once the log entry has been written, microcontroller 800 returns to step 1000 and proceeds to step 1002, where it loops until next dosing interval begins.

At block 1034, microcontroller 800 inserts a delay period to give the patient some time to replace dosing drawer 832 without being instructed to do so. A suitable delay period might be five or ten minutes.

At block 1036, microcontroller 800 provides an audio or visual message to the patient reminding him or her to replace dosing drawer 832. Such a message may take a form such as, "please remember to replace the dosing tray."

At block 1016, microcontroller 800 evaluates whether the dosing interval started in block 1002 above has expired. So long as that dosing interval has not expired, as indicated by the N branch from block 1016, microcontroller 800 returns to block 1014. Accordingly, so long as the patient has not removed dosing drawer 832 and the dosing interval has not expired, microcontroller 800 loops between blocks 1014 and 1016 until the dosing interval expires. When the dosing interval expires, microcontroller 800 proceeds along the Y branch from block 1016 to block 1018.

If the dosing interval expires without the patient removing dosing drawer 832, then the patient has missed the dose. At block 1018, the patient has missed the dose and microcontroller 800 provides a suitable message over visual means 802 or audio means 804. Such a message might indicate that the patient has missed the dose and that the dose is no longer accessible. The message might also indicate to the patient when the next dose period will begin.

At block 1020, microcontroller 800 writes a log entry for the missed dose. Such a log entry might include the time and date at which the dose period expired, perhaps along with the sequence number within a series of doses. For example, the log entry could indicate that on a given day, the patient has missed the third dose of a series of five doses.

At block 1022, microcontroller 800 can alert central station 100 that the patient has missed a dose. This alert to central station 100 enables personnel at that station to take appropriate action because the patient has missed a recent dose. Also in block 1022, microcontroller 800 can provide auxiliary alerts to the patient such as lights, buzzers or etc. that notify the patient that he or she has missed a dose. Microcontroller 800 can also instruct the patient to contact central station 100 if missed doses are critical to the patient's medication regime.

At block 1024, microcontroller 800 locks dosing drawer 832 to prevent any further access to dosing drawer 832, since the dosing interval has expired. This locking process prevents the patient from taking successive doses of medication too close together.

At block 1026, microcontroller 800 activates trap door 836 at the bottom of dosing drawer 832, thereby dropping the dose of medication contained in dosing drawer 832 into recovery drawer 832. Once dropped into recovery drawer 834, the dose of medication is no longer accessible to the patient. In this manner, microcontroller 800 prevents the patient from inadvertently double-dosing on two successive doses of medication. Otherwise, when the next dosing interval arrives, the next dose of medication would be dropped into dosing drawer 832 along with the previous dose. If the patient took two doses at once, severe consequences could result.

Once the dose of medication has been removed from dosing drawer 832, microcontroller 800 proceeds to block 1028. At block 1028, dosing drawer 832 is unlocked because it is now empty and therefore poses no medication hazard to the patient Once dosing drawer 832 has been unlocked, microcontroller 800 returns to block 1000 and awaits the beginning of the next dosing interval, as indicated in block 1002.

Figure 16:
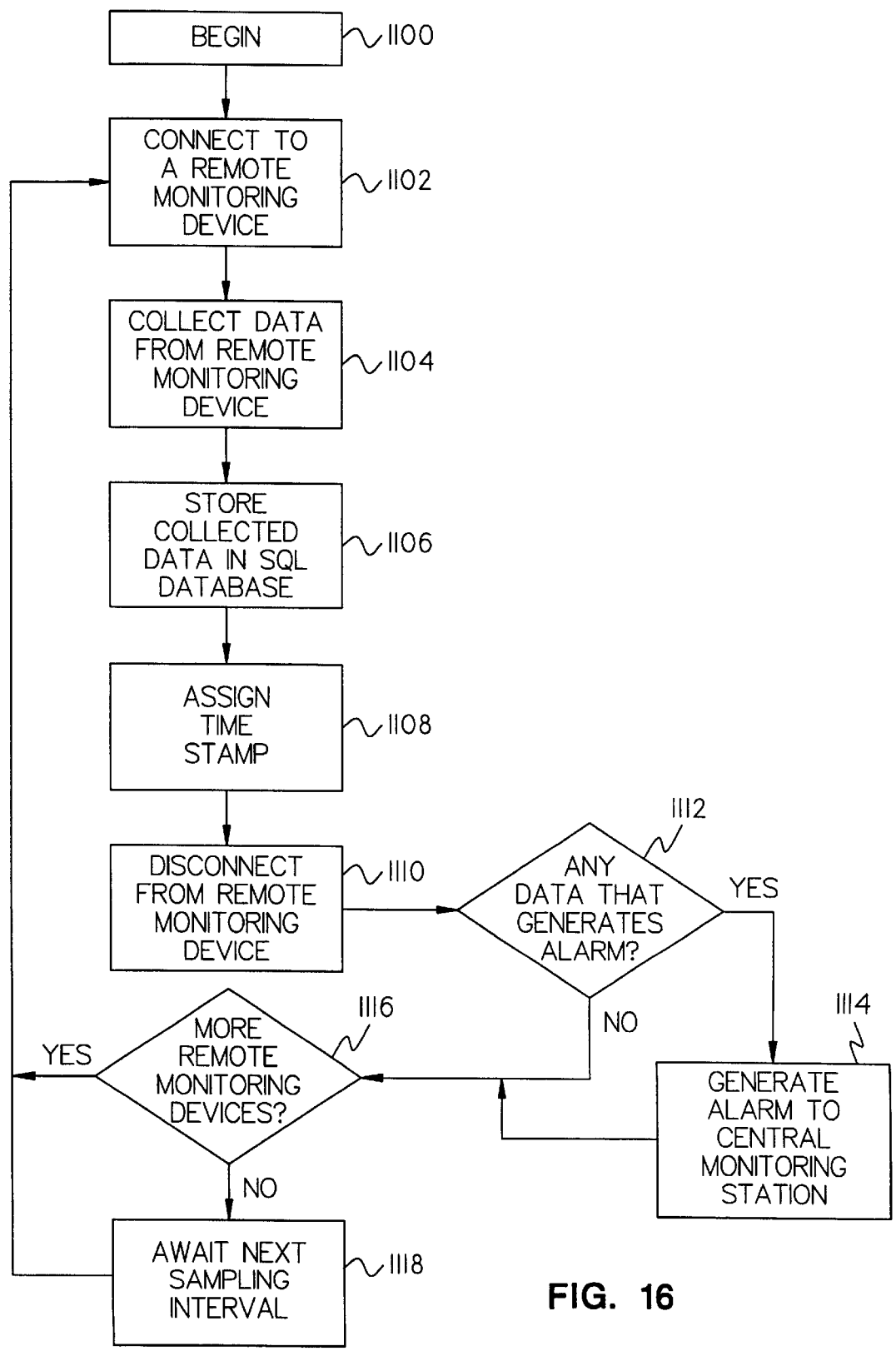
FIG. 16 is a flow chart illustrating the processing performed by the software running on the PC illustrated in FIGS. 2 and 4.

FIG. 16 is a flow chart illustrating the processing performed by the software running aboard PC 202 as illustrated in FIGS. 2 and 4. As described above, each remote site 200 includes a local PC 202. Periodically, PC 202 enters a sampling interval, wherein it polls each monitoring device or sensor at remote site 200 to sample data from those devices and sensors. PC 202 enters data from each of the devices and sensors into a local database maintained aboard PC 202.

Processing begins at block 1100 and proceeds to block 1102 to connect to one of the devices or sensors located at remote site 200. Exemplary monitoring devices and sensors are biosensors 206, environmental sensors 204, patient monitoring unit 214, door sensor 220, window sensor 222, motion detector 224, and non-motion detector 240.

At block 1104, data is collected or sampled from the device or sensor that was accessed in block 1102 above. At block 1106, the collected data is stored in a local SQL database maintained by PC 202 at the remote site 200. At block 1108, a time stamp is generated and assigned to the data stored in the SQL database in block 1106 above. At block 1110, PC 202 disconnects from the given device or sensor connected to in block 1102 above, thereby terminating the current session with that monitoring device or sensor until the next sampling interval arrives.

At block 1112, PC 202 examines the data that was sampled and collected from the monitoring device or sensor, and determines whether any of that data represents a patient condition that should generate an alarm. If so, PC 202 proceeds to block 1114 to generate a suitable alarm signal to central station 100. If not, PC 202 proceeds to block 1116 to sample a next monitoring device or sensor, if any, that is yet to be sampled in the current sampling interval.

At block 1114, PC 202 generates an appropriate alarm to the central station 100. After generating this alarm, PC 202 proceeds to block 1116.

At block 1116, PC 202 evaluates whether there are more monitoring devices or sensors to be sampled during the current sampling interval. If so, PC 202 returns to block 1102 to connect to another monitoring device or sensor. If there are no more monitoring devices or sensors to be sampled during this sampling interval, PC 202 proceeds to block 1118, where it delays to await the next sampling interval. When the next sampling interval begins, PC 202 returns to block 1102 to connect to and sample the first monitoring device or sensor for that sampling interval.

FIG. 17 is a diagram of an exemplary database record storing the data collected during the execution of the software illustrated by the flowchart in FIG. 16. Particularly, FIG. 17 illustrates the database record for storing the data collected at block 1106.

The database record contains a timestamp data field to indicate the time of the sampling interval. According to different aspects of the invention, the time stamp is associated with all of the entries in the database record, or individual time-stamps are associated with each of the entries in the database record.

The rest of the entries in the database are determined by the particular monitoring equipment chosen to equip a given remote monitoring site 200, and FIG. 17 illustrates an exemplary configuration. In this exemplary configuration, an entry is provided for door sensor 220, window sensor 222, motion detector 224, non-motion detector 240, the data from biosensors 206, the data from environmental sensors 204, and the data from patient monitoring unit 214. The entry for the data from biosensors 206 can be subdivided into sub-data fields, with each sub-data field corresponding to one of biosensors as illustrated in FIG. 7. For example, the database record provides a data field for the oxygen saturation level as provided by oxygen saturation sensor 700, a data field for a digitized ECG waveform as provided by ECG sensor 702, and data fields for readings from stethoscope 704, glucometer 706, and spirometer 708.

In an exemplary embodiment, the data stored from environmental sensors 204 is divided into sub-data fields in the same manner as the biosensor data. For example, the database record provides a sub-data field for storing the room temperature from room temperature sensor 710, a sub-data field for the room humidity from humidity sensor 712, and a sub-data field for the barometric pressure from barometer 711. The database record also provides additional sub-data fields for the carbon monoxide level from carbon monoxide sensor 714, and for the air quality signal from smoke detector 716. Likewise, the data provided by patient monitoring unit 214 can be subdivided and assigned to sub-data fields. For example, the pulse rate, the respiration rate, and the blood pressure data can be stored in separate sub-data fields for convenience.

It will be understood that the database record shown in FIG. 17 is exemplary only, with actual database records varying depending on the specific equipment provided at a given remote site 200.

As the software illustrated in FIG. 16 iterates through several sampling intervals, PC 202 generates and populates one copy of the database record illustrated in FIG. 17. After several sampling intervals, PC 202 generates a time-stamped patient record, with each record corresponding to the exemplary database record illustrated in FIG. 17. This database record can then be imported into a suitable, commercially available database application, and the data can then be analyzed to isolate trends in patient data or to identify patient hazards.

The database record of FIG. 17 also illustrates the parameters that PC 202 uses in block 1112 of FIG. 16 to determine whether it should generate an alarm. For example, by reviewing the door status and window status, PC 202 can determine whether anyone has had unauthorized access to the patient's room. By checking the motion detector status and the non-motion detector status, PC 202 can determine whether the patient is exhibiting an expected level of physical activity. By examining the database record responding to the biosensor data, PC 202 can determine whether the patient's vital signs are within tolerances. If one or more of the patient's vital signs are out of tolerance, then PC 202 can generate an appropriate alarm to central station 100. The same considerations apply, for example, to the data from patient monitoring unit 214. Likewise, PC 202 can evaluate the data provided by environmental sensor 204 to ensure that the climatic conditions within the patient's room are within tolerance.

Figure 18:
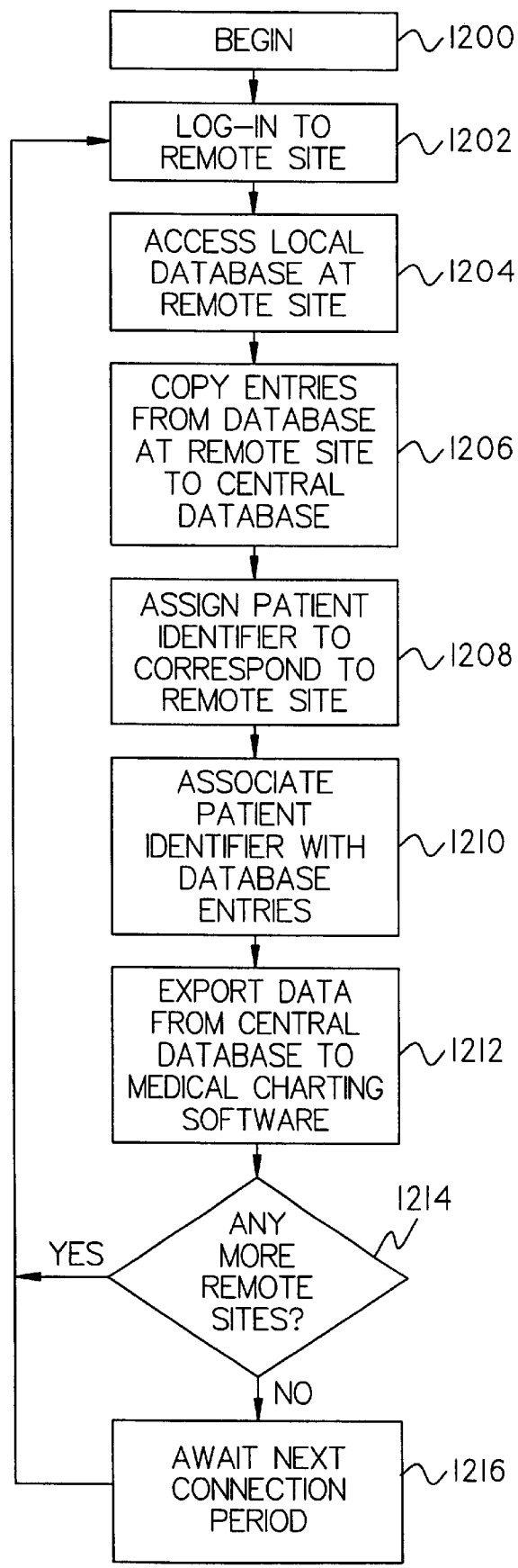
FIG. 18 is a flowchart of the software running aboard the server.

FIG. 18 is a flowchart of the software running on server 402. As stated above, server 402 is located at central station 100. Periodically, server 402 enters a sampling interval, wherein server 402 connects to each of the remote sites 200 to download the entries in the local database maintained by PC 202 at each remote site 200. When server 402 accesses a given remote site 200, server 402 accesses the entries made in the local database maintained by PC 202 at the given remote site 200. Server 402 then downloads those local database entries into a central database maintained by server 402.

Processing starts at begin block 1200 and proceeds to block 1202, where server 402 connects with and logs into a given remote site 200 to access the local database maintained there. At block 1204, server 402 accesses the local database at the remote site 200. At block 1206, server 402 copies the entries from the local database at the remote site 200, and transfers those entries into a central database maintained by server 402.

At block 1208, server 402 generates and assigns a unique patient identifier to correspond to the remote site 200 that server 402 is currently accessing. This patient identifier serves to indicate which remote site 200 is associated with a given group of database entries in the central database maintained by server 402. At block 1210, server 402 associates the given patient identifier with the group of database entries retrieved during block 1206 above.

In block 1212, server 402 exports the data from the central database to the medical charting software, shown in FIG. 4. At block 1214, server 402 checks to see if any remote sites 200 remain to be accessed in the given sampling interval. If so, then server 402 returns to block 1202 to log into the next remote site 200. If not, then server 402 proceeds to block 1216 and awaits the next sampling interval, at which time server 402 once again logs into each of the remote sites 200 and downloads new database entries.

Figure 19:
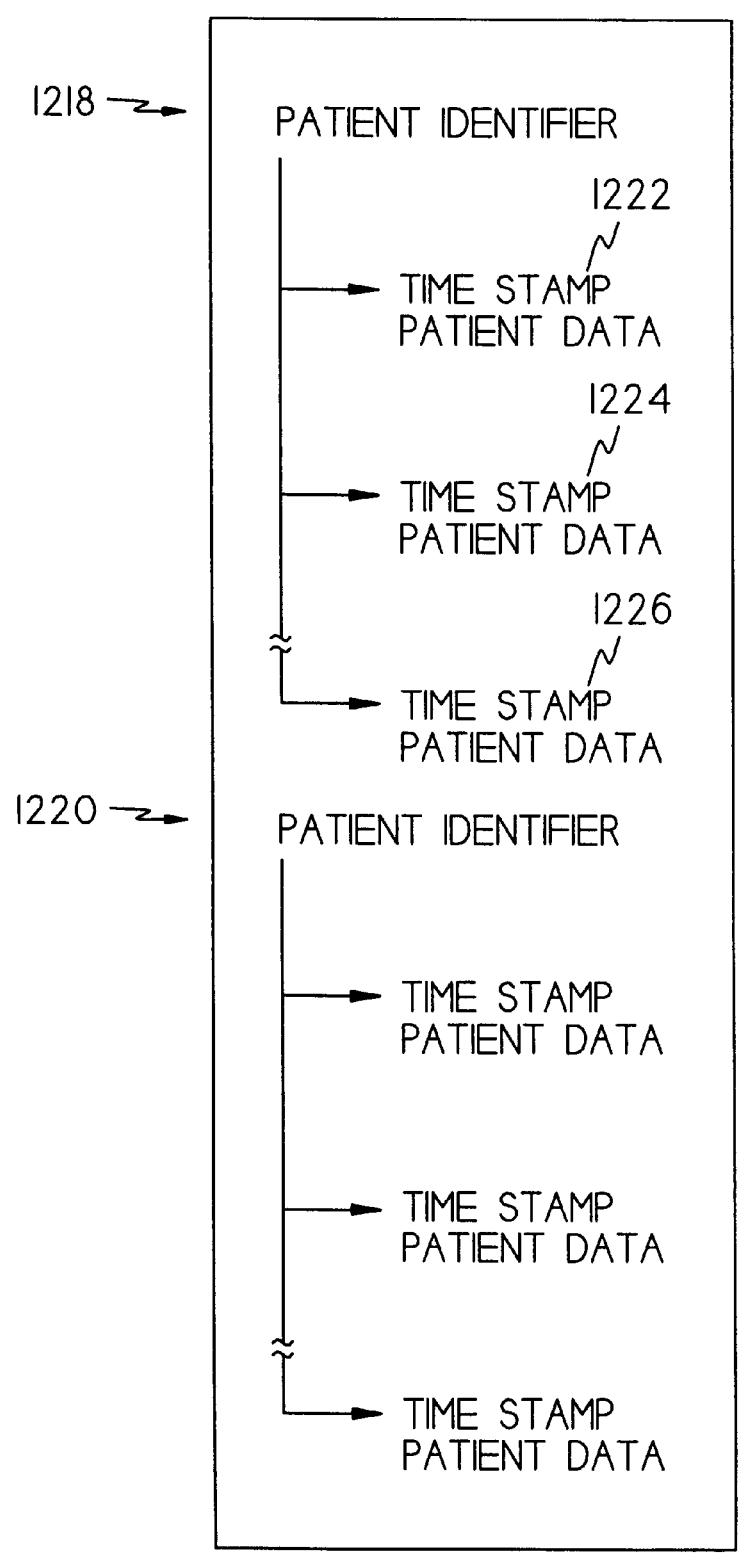
FIG. 19 is a diagram of an exemplary database record maintained by the server.

FIG. 19 is a diagram of an exemplary database record maintained on server 402, shown in FIG. 2. Server 402 generates and populates the exemplary database record shown in FIG. 19 as it logs into remote sites 200 during a given sampling interval.

Reference numerals 1218 and 1220 designate individual records corresponding to two patient identifiers, which are described above in FIG. 18. The patient identifier corresponds to a given remote site 200. For example, a first patient may reside at a first remote site 200a and be assigned a first unique patient identifier number. A second patient may reside at a second remote site 200b and be assigned a second unique patient identifier number.

Within an exemplary patient identifier record, such that indicated by reference numeral 1218, the database record provides a plurality of sub-data fields, as indicated by reference numerals 1222, 1224, and 1226. Each of these three sub-data fields can contain at least two data fields, one data field for a time stamp, and a second data field for patient data. The timestamp indicates the time at which the patient data field is populated. The contents of the patient data field depends upon the configuration of the given remote site 200 corresponding to the patient identifier.

The database record illustrated in FIG. 19 provides an exemplary patient data field. However, it should be noted that different remote sites 200 are configured differently depending on the requirements of a given patient.

Accordingly, the contents of the database field corresponding to that remote site 200 varies. It should also be noted that although three timestamp records are shown in FIG. 19, as server 402 executes successive sampling intervals, additional time-stamped records will be appended beneath the exemplary patient identifier data fields 1218 and 1220. In addition, although FIG. 19 shows two patient identifier records for simplicity, the exemplary database record can be extended to accommodate any number of remote sites 200 with a corresponding number of unique patient identifiers.

Figure 20:
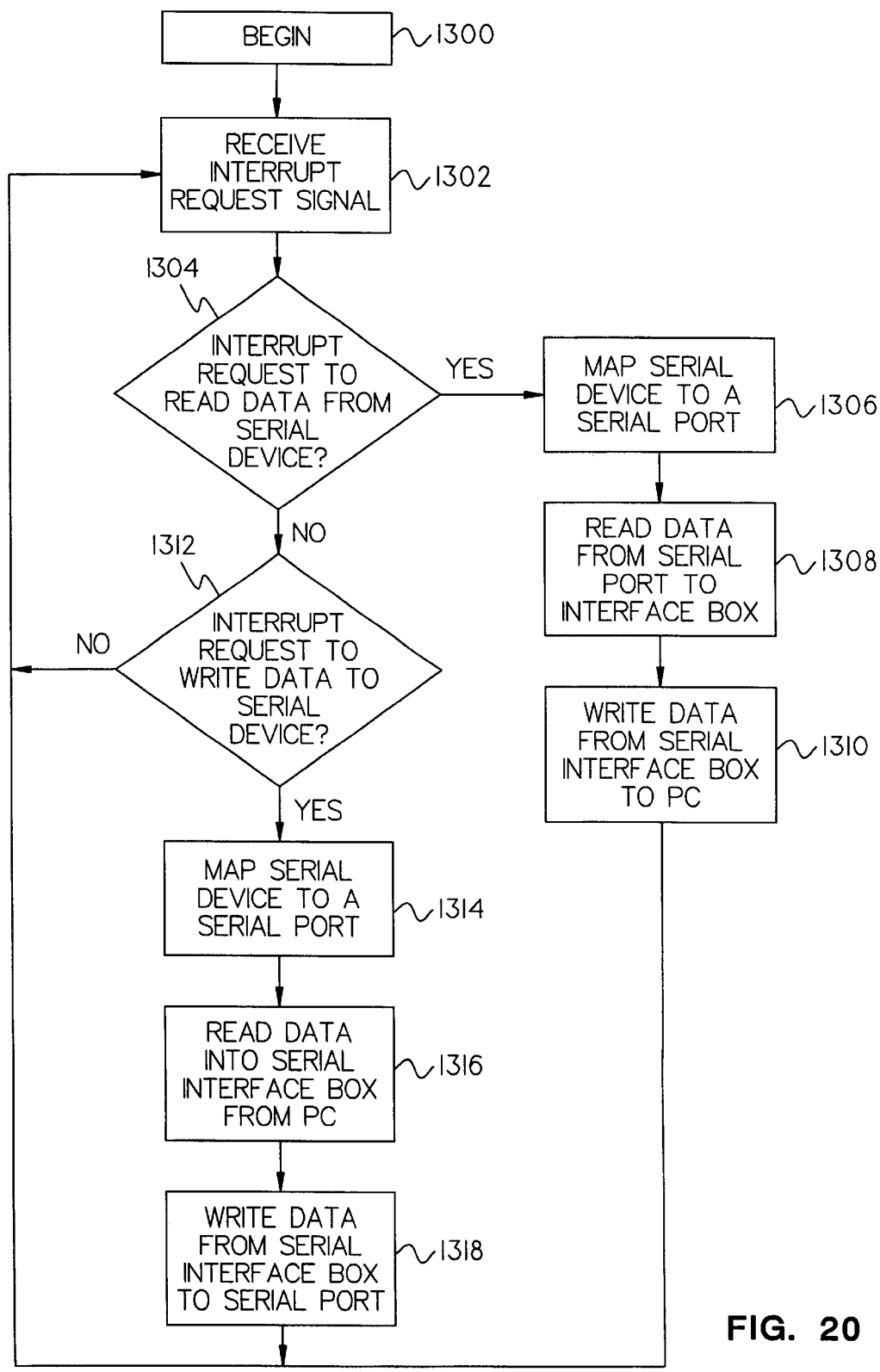
FIG. 20 is a flowchart of the software executing on the serial interface box.

FIG. 20 is a flowchart of the software executing on serial interface box 208. Serial interface box 208 serves to connect PC 202 to the several multiplexed serial monitoring devices and sensors shown in FIG. 2. The software shown in FIG. 20 serves to regulate the flow of data between PC 202 and the several multiplexed serial devices and sensors.

Processing begins at block 1300 and proceeds to block 1302 to await an interrupt request (INTR) signal. Upon receiving an INTR signal, processing proceeds to block 1304, where serial interface box 208 evaluates whether the INTR signal represents a request to read data from one of the multiplexed serial devices. If so, serial interface box 208 proceeds to block 1306 to service the INTR signal as a request to read. If not, serial interface box 208 proceeds to block 1312, where it evaluates whether the INTR signal represents a request to write data from one of the multiplexed serial devices. If so, serial interface box 208 proceeds to block 1314 to service the INTR signal as a request to write. If not, the INTR signal was either erroneous or intended for some purpose other than executing reads or writes from/to the multiplexed serial devices, and serial interface box 208 loops back to block 1302 to await the next INTR signal.

Blocks 1306–1310 represent the general steps of an interrupt service routine (ISR) that services requests from PC 202 to read data from one of the multiplexed serial devices or sensors coupled to serial interface box 208. For example, PC 202 may generate an interrupt to read the data from biosensors 206, environmental sensors 204, patient monitoring unit 214, medication dispensing unit 212, or the other multiplexed devices coupled to serial interface unit 208.

In block 1306, serial interface box 208 identifies the serial device from which PC 202 is reading, and maps that device to a corresponding port of serial interface box 208. At block 1308, serial interface box 208 reads the data from the serial port. Depending on the size of the data, this data can be either buffered or latched to await forwarding to PC 202. Buffering refers to storage in memory for later access; latching refers to temporary storage, such as in a flip-flop. In block 1310, the data read from the serial port is written to PC 202, either from a buffer or from transceiver latches.

Blocks 1314–1318 represent the general steps of an interrupt service routine (ISR) that services requests from PC 202 to write data to one of the serial devices or sensors coupled to serial interface box 208. For example, PC 202 may generate an interrupt to write command or configuration data to environmental control system 210, patient monitoring unit 214, medication dispensing unit 212, or other devices coupled to serial interface unit 208.

In block 1314, serial interface box 208 identifies the serial device to which PC 202 is writing, and maps that serial device to a corresponding serial port of serial interface box 208. At block 1316, serial interface box 208 reads data from PC 202. Depending on the size of the data, this data can be either buffered or latched to await forwarding to the serial device. At block 1318, the data is written from serial interface box 208 to the serial device identified in block 1306.

Figure 21:
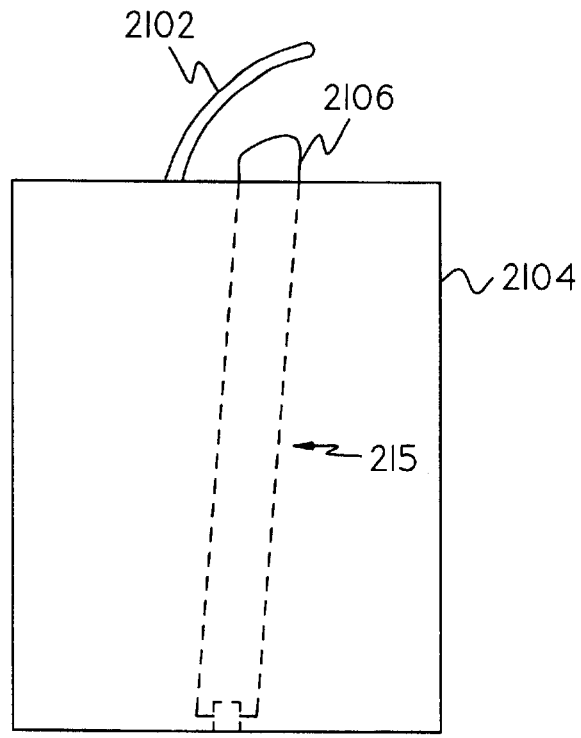
FIG. 21 is an exemplary side view of the connector as connected to a cradle provide by the patient monitoring unit.

FIG. 21 is an exemplary side view of connector 215 as connected to patient monitoring unit 214. In an exemplary and not limiting embodiment, connector 215 provides a male coupling, and patient monitoring unit 214 provides a cradle 2104, which is a complementary female coupling. Cable 2102 runs between connector 215 and sensor 218 housed in garment 216 (FIGS. 5 and 6). The contents of cable 2102 depend upon the types of sensors 218 housed in garment 216. In an exemplary embodiment, cable 2102 can contain conductors corresponding to an ECG sensor and a blood pressure cuff. In additional embodiments, cable 2102 can contain conductors corresponding to speaker 614 and microphone 616 shown in FIG. 6. Loop 2106 can be joined to connector 215 so as to extend from cradle 2104. Loop 2106 allows the patient to disconnect connector 215 by pulling on loop 2106, rather than cable 2102, thus preventing the patient from fatiguing the connections between cable 2102 and connector 215 by pulling on cable 2102.

Figure 22:
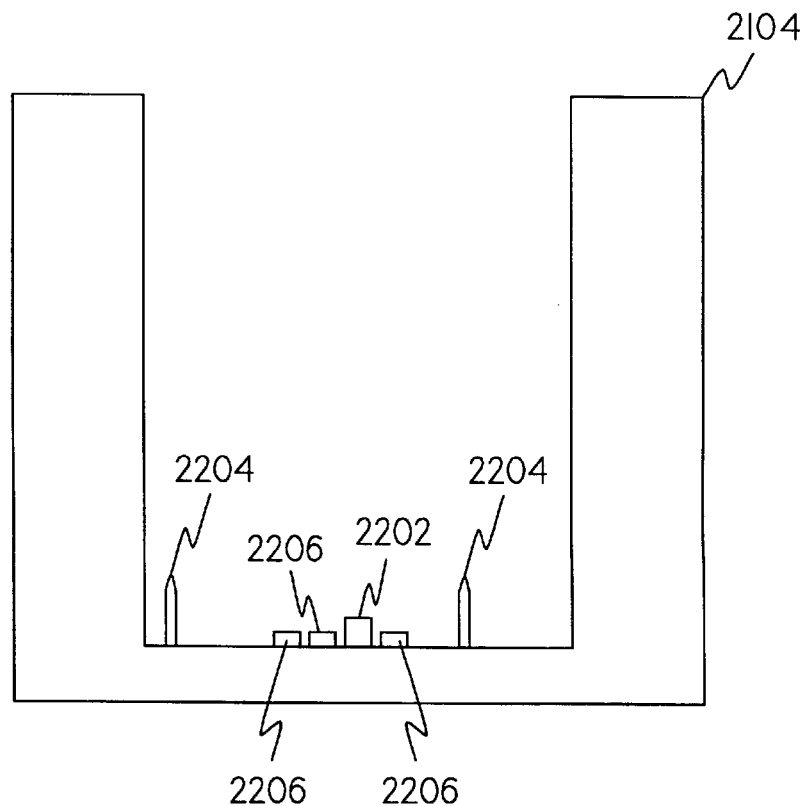
FIG. 22 is an exemplary front view of the cradle shown in FIG. 22, with the connector removed.

FIG. 22 is an exemplary front view of cradle 2104 shown in FIG. 22, with connector 215 removed. Cradle 2104 is shaped to receive connector 215, and the U-shape shown in FIG. 22 is exemplary rather than limiting. One or more alignment pins 2204 can be provided at the bottom of cradle 2104 to ensure that connector 215 is coupled properly to cradle 2104. Alignment pin 2204 can be keyed to engage complementary structure provided in connector 215, such as one or more suitable apertures. In an exemplary embodiment shown in FIG. 22, cradle 2104 provides at least one electrode 2206 to connect to connector 215. For example, electrode 2206 can be an electrical lead connecting to an ECG monitor of patient monitoring unit 214. If garment 216 is equipped with a blood pressure cuff, then cradle 2104 provides pressure connector 2202 to couple the blood pressure cuff in garment 216 with patient monitoring unit 214.

Figure 23:
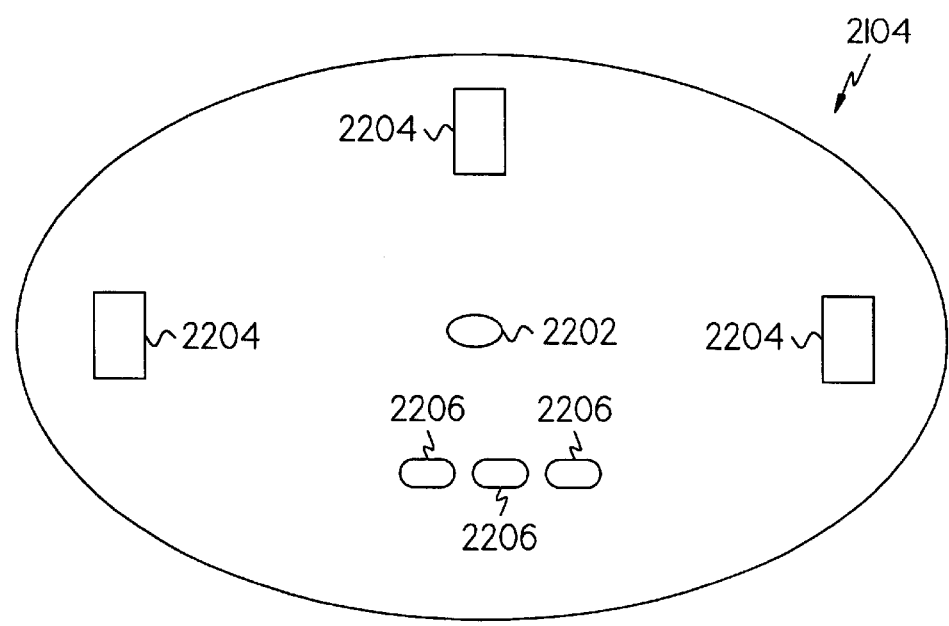
FIGS. 23 and 24 are top views of alternate embodiments of the cradle shown in FIG. 22.
Figure 24:
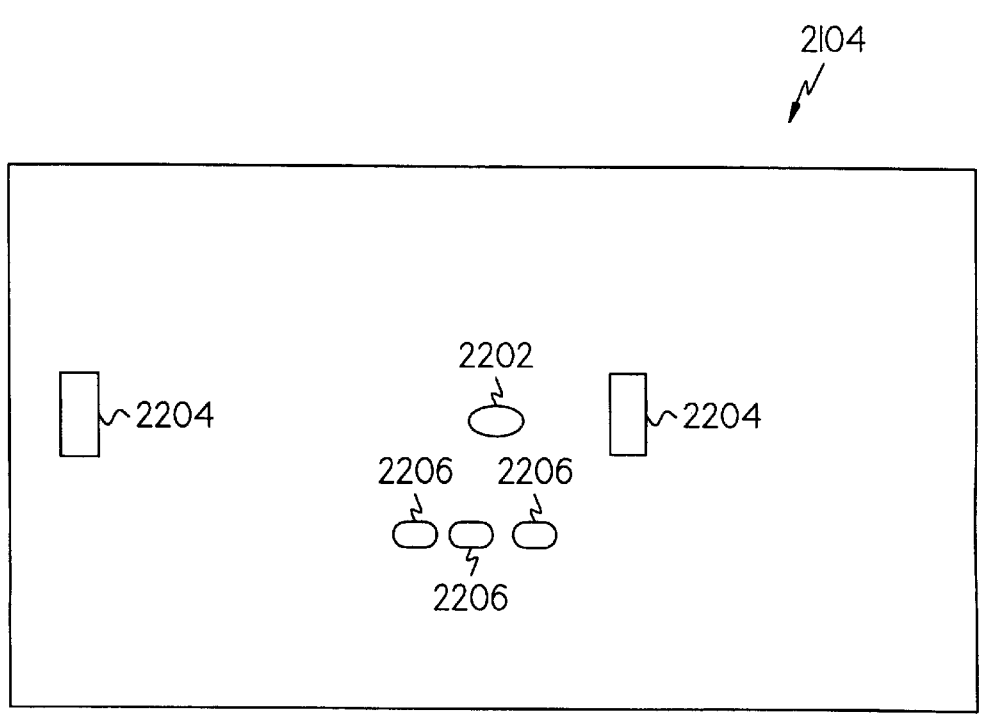

FIGS. 23 and 24 are top views of cradle 2104 according to alternate embodiments of the invention. In FIG. 23, cradle 2104 has a ovoid shape, and provides an exemplary configuration of alignment pins 2204, electrodes 2206, and pressure connector 2202 as described in FIG. 22 above. In FIG. 24, cradle 2104 has a rectangular shape, and provides another exemplary configuration of alignment pins 2204, electrodes 2206, and pressure connector 2202 as described in FIG. 22 above. It should be understood that FIGS. 21–24 illustrate connector 215 that uses a hard-wired, physical connection to patient monitoring unit 214. If an RF link is used rather than a hard-wired connection, then the RF link will substitute for the structure shown in FIGS. 21–24.

The exemplary embodiments shown in FIGS. 21–24 feature a push-pull connection for ease of connection/disconnection by the patient. However, if patient dexterity is not a concern, then fluidic/pneumatic connectors are available from LEMO-USA of Santa Rosa, Calif., which connectors may be suitable for pressure connector 2202 shown above. Also, TronoMed®, Inc. of San Juan Capistrano, Calif. markets a TronoMate® connector that may be suitable for electrodes 2206 above.

Figure 25:
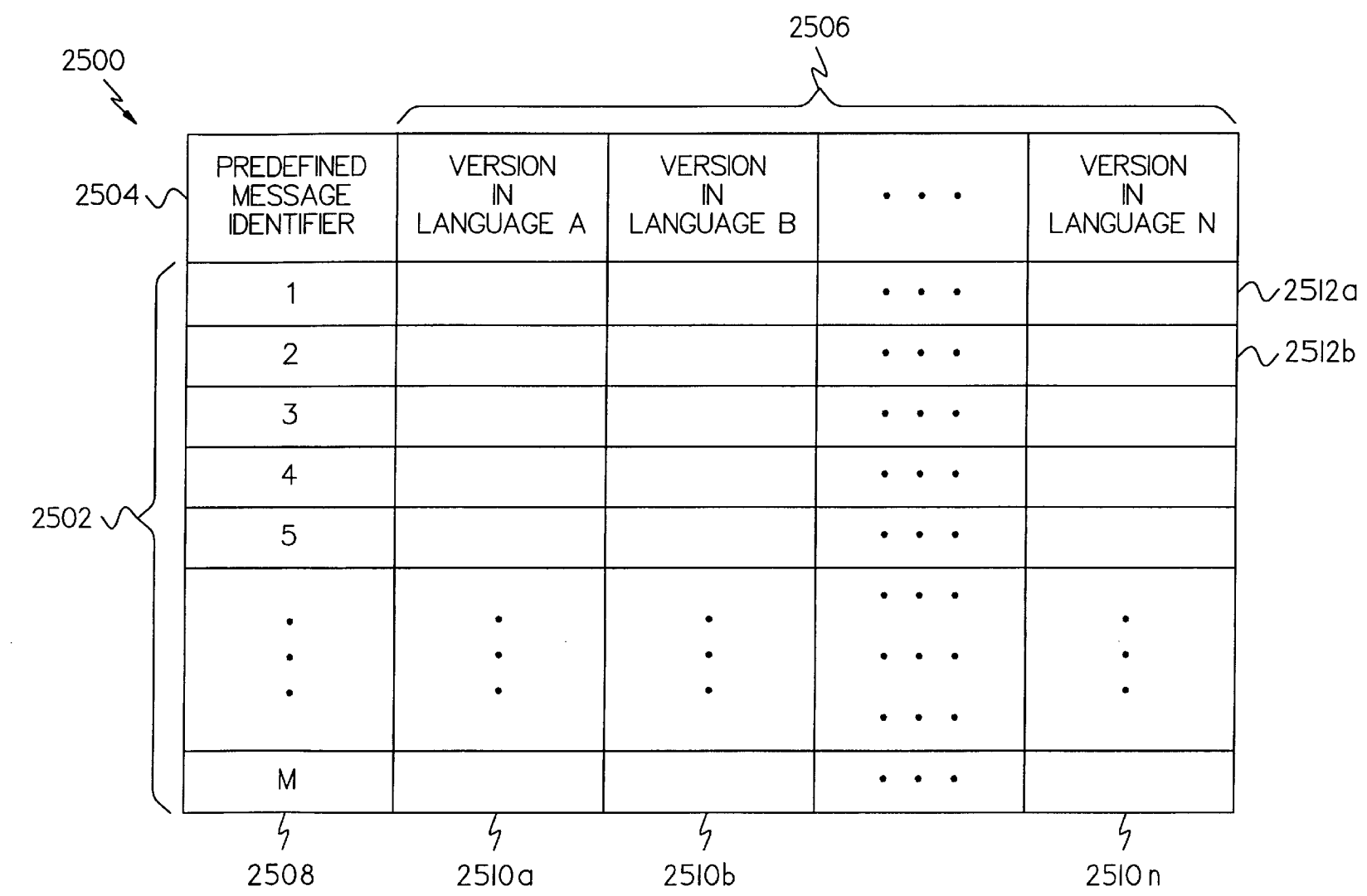

FIG. 25 is a diagram of an exemplary data structure 2500 used with medication dispensing unit 212 shown in FIG. 2. Data structure 2500 enables medication dispensing unit 212 to communicate effectively with a patients speaking a plurality of different languages.

In an exemplary and nonrestrictive embodiment, data structure 2500 can be arranged as a matrix having a plurality of columns and a plurality of rows. Header row 2504 is shown merely to describe the contents of columns beneath each entry in header row 2504, and may or may not be included in data structure 2500. Column 2508 stores message identifiers, while columns 2510a–2510n store messages corresponding to those identifiers in a plurality of languages.

In the exemplary embodiment shown, column 2508 contains a sequence of unique identifiers, with one identifier corresponding to each message supported by medication dispensing unit 212. Medication dispensing unit 212 plays these messages over audio means 804 and display means 802 (see FIG. 8) under the control of microcontroller 800. By playing selected messages, medication dispensing unit 212 can at least greet the patient, instruct the patient on how to take medication, remind the patient to take a dose, alert the patient when he or she misses a dose, and notify the patient when to take the next dose.

In the exemplary embodiment shown, columns 2510a–2510n stores text messages in a plurality of different languages. The number n of columns 2510a–2510n varies according to the number of languages supported by medication dispensing unit 212. For example, column 2510a might contain English versions of the messages corresponding to the message identifiers listed in column 2508. Similarly, column 2510b might contain German versions of the same messages, while the remaining columns 2510c–2510n might contain versions in still more languages.

In the above manner, row 2512a contains versions of the message corresponding to message identifier 1 in n different languages, with one message in each language contained in one each of the columns contained in row 2512a. Similarly, row 2512b contains versions of the message corresponding to message identifier 2 in n different languages, with one message in each language contained in one each of the columns contained in row 2512b, and so on through each row in data structure 2500.

FIG. 26 is a diagram of an exemplary data structure 2600 that can be used in conjunction with data structure 2500 shown in FIG. 25 to enable medication dispensing unit 212 to provide messages in several different languages. In the exemplary embodiment shown in FIG. 26, data structure 2600 is a matrix mapping a plurality of events in column 2602 to a plurality of message identifiers 2604.

Column 2602 contains an entry for each event associated with a message. Exemplary events might include a greeting to the patient, instructions on taking medication, a reminder to return dosing drawer 832, an alert that the patient has missed a dose, and so on. For purposes of illustration only, the numbers 1–M in column 2602 represent these exemplary events conceptually and symbolically. For example, event #1 might command medication dispensing unit 212 to issue a greeting to the patient, event #2 might command medication dispensing unit 212 to provide prescription dosing instructions, and so on. Also, the exemplary entries shown in column 2604 are strictly for illustration purposes, and the entries in column 2604 can vary in implementation.

Column 2604 contains a message identifier corresponding to each entry in column 2602. The message identifiers in column 2604 serve as indices into data structure 2500 shown in FIG. 25, and correspond to the entries in column 2508 of data structure 2500. For example, if event #1 in data structure 2600 represents a command to issue a greeting to the patient, then data structure 2600 maps event #1 to message identifier #5. Message identifier #5 selects a row in data structure 2500 shown in FIG. 25. Given the row selected in data structure 2500, microcontroller 800 can select the correct language for the patient by traversing columns 2510a through 2510n.

Medication dispensing unit 212 is programmed using data structures 2500 and 2600 in the following manner. Using the data structure 2600, medical personnel configure each message supported by medication dispensing unit 212 by associating each event in column 2602 of data structure 2600 with a corresponding message identifier in column 2604. As stated above, the message identifiers in column 2604 index into data structure 2500. For example, nurses or orderlies might configure such messages as the greetings, warnings, or reminders, while pharmacists or physicians might configure such messages as the medication dose instructions or other directions for the patient.

An important feature of medication dispensing unit 212 is its ability to allow programming in a first language, while providing patient instructions in a second language. For example, medical personnel might program medication dispensing unit 212 by reviewing a dictionary of messages in a first language, such as English. As the personnel peruse and locate appropriate messages, they assign those messages to specific events by manipulating data structure 2600. When medication dispensing unit 212 is fully programmed with messages for each event, then it is sent on-site to remote site 200.

When medication dispensing unit 212 arrives on-site, either the medical personnel or the patient can select the language that medication dispensing unit 212 uses to provide messages on display means 802 and audio means 804. The language used on-site may be the same or a different language as that used to program medication dispensing unit 212. The linkage between column 2604 in data structure 2600 and column 2508 in data structure 2500 provides this flexibility. This linkage is not language-specific; instead, it relies on logical or conceptual linkage between the events listed in column 2602 of data structure 2600 and the multilingual messages shown in column 2510a through column 2510n of data structure 2500.

In a further embodiment, medication dispensing unit 212 can support customized messages, in addition to providing a built-in dictionary of messages. In this manner, authorized medical personnel can associate a custom message with selected events, as discussed above. As a security precaution, however, microcontroller 800 can be configured to require entry of a password or other security code before allowing entry of customized messages. By restricting dissemination of the password or security code, medical personnel can reduce the risk that messages will be improperly changed.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. For example, the above description referred several times to electrical circuits, especially for controlling the various components of medication dispensing unit 212. However, pneumatic control circuits could be substituted for these electrical control circuits without departing from the scope of the invention.

What is claimed:

1. A medication dispensing unit comprising:
   a removable carousel defining a plurality of compartments, each of the compartments adapted to store a dose of medication;

a housing including a surface adapted to receive the carousel, the housing defining a receptacle and an access aperture communicating between the receptacle and the surface adapted to receive the carousel, a first one of the compartments positioned to communicate with the receptacle through the access aperture;

dosing drawer being positionable within the receptacle and in communication with the access aperture to receive the dose of medication from the first compartment through the access aperture, the dosing drawer including a normally-closed trapdoor that when opened, allows the dose of medication in the drawer to drop out of the dosing drawer;

a recovery drawer being positionable within the receptacle and in communication with the dosing drawer through the trapdoor to receive the dose of medication from the dosing drawer when the trapdoor is opened;

means for rotating the carousel to position a second one of the compartments to communicate with the receptacle through the access aperture;

a microcontroller coupled to control the opening of the trapdoor and the operation of the rotation means, the microcontroller being programmed to:

define a dosing period during which the patient may access the medication in the dosing drawer;

determine that the patient has not accessed the dosing drawer within the dosing period and to open the trapdoor at the end of the dosing period to drop the dose of medication from the dosing drawer into the recovery drawer; and lock the recovery drawer.

2. The medication dispensing unit of claim 1, further comprising audio means coupled to the microcontroller for alerting the patient to take the dose of medication during the dosing period, and visual means coupled to the microcontroller for alerting the patient to take the dose of medication during the dosing period.

3. The medication dispensing unit of claim 2, wherein at least one of the audio means and the visual means are configured to provide medication dose instructions to the patient.

4. The medication dispensing unit of claim 1, wherein the microcontroller is programmed to log data representing a missed dose of medication when medication is dropped into the recovery drawer.

5. The medication dispensing unit of claim 1, further comprising clock means coupled to the microcontroller.

6. The medication dispensing unit of claim 1, further comprising a port coupled to the microcontroller to allow an external computer to access the microcontroller.

7. The medication dispensing unit of claim 1, wherein the microcontroller is linked to a central station, and wherein the microcontroller is conigured to contact the central station if a dose is missed.

* * * * *